(12) United States Patent
Avila et al.

(10) Patent No.: US 11,119,565 B2
(45) Date of Patent: *Sep. 14, 2021

(54) OPTICAL DETECTION AND ANALYSIS OF BONE

(71) Applicant: Samsung Electronics Company, Ltd., Gyeong gi-Do (KR)

(72) Inventors: Santiago Ortega Avila, San Jose, CA (US); Sajid Sadi, San Jose, CA (US); Bogdana Rakova, Mountain View, CA (US)

(73) Assignee: SAMSUNG ELECTRONICS COMPANY, LTD., Suwon (KR)

( * ) Notice: Subject to any disclaimer, the term of this patent is extended or adjusted under 35 U.S.C. 154(b) by 1265 days.

This patent is subject to a terminal disclaimer.

(21) Appl. No.: 14/997,432

(22) Filed: Jan. 15, 2016

(65) Prior Publication Data
US 2016/0206206 A1    Jul. 21, 2016

Related U.S. Application Data

(60) Provisional application No. 62/105,163, filed on Jan. 19, 2015.

(51) Int. Cl.
*G06F 3/01* (2006.01)
*G06F 1/16* (2006.01)
(Continued)

(52) U.S. Cl.
CPC .............. *G06F 3/011* (2013.01); *G06F 1/163* (2013.01); *G06F 3/017* (2013.01); *G06F 3/042* (2013.01); *G06F 21/32* (2013.01)

(58) Field of Classification Search
None
See application file for complete search history.

(56) References Cited

U.S. PATENT DOCUMENTS 6,475,153 B1 * 11/2002 Khair ................. A61B 5/02007
                                                         600/485
6,720,984 B1    4/2004 Jorgensen
(Continued)

FOREIGN PATENT DOCUMENTS

CN      204965329 U    1/2016
JP      2002361576 A   12/2018
(Continued)

OTHER PUBLICATIONS

Extended European Search Report for Application No. 16740371.6-1216, dated Apr. 10, 2018.
(Continued)

*Primary Examiner* — Luther Behringer
(74) *Attorney, Agent, or Firm* — Baker Botts L.L.P.

(57) ABSTRACT

In one embodiment, a method may include outputting one or more sensor signals from an electronic device into a portion of a user's body, and detecting one or more deflected signals from the one or more sensor signals. The method may include detecting a bone structure of the user's body based on the one or more deflected signals. Then, the method may include determining a user measurement based on the one or more deflected signals, the health measurement being adjusted by the detected bone structure.

19 Claims, 22 Drawing Sheets

(51) Int. Cl.
*G06F 21/32* (2013.01)
*G06F 3/042* (2006.01)

(56) References Cited

U.S. PATENT DOCUMENTS

| | | | | |
|---|---|---|---|---|
| 6,747,632 | B2 * | 6/2004 | Howard | G06F 3/014 |
| | | | | 345/157 |
| 7,340,077 | B2 | 3/2008 | Gokturk | |
| 7,519,223 | B2 | 4/2009 | Dehlin | |
| 7,610,080 | B1 | 10/2009 | Winchester | |
| 8,292,833 | B2 * | 10/2012 | Son | A61B 5/681 |
| | | | | 600/595 |
| 8,351,651 | B2 | 1/2013 | Lee | |
| 8,447,704 | B2 | 5/2013 | Tam | |
| 8,581,856 | B2 | 11/2013 | Benko | |
| 8,588,467 | B2 | 11/2013 | Yoon | |
| 8,988,345 | B2 | 3/2015 | Ackerman | |
| 9,389,694 | B2 | 7/2016 | Ataee | |
| 9,772,684 | B2 | 9/2017 | Shi | |
| 10,362,944 | B2 * | 7/2019 | Avila | A61B 5/4504 |
| 2002/0024500 | A1 | 2/2002 | Howard | |
| 2002/0072786 | A1 | 6/2002 | Gordon | |
| 2005/0021110 | A1 | 1/2005 | Maschke | |
| 2005/0107849 | A1 | 5/2005 | Altshuler | |
| 2009/0174578 | A1 * | 7/2009 | Taki | G01B 11/03 |
| | | | | 341/20 |
| 2010/0042031 | A1 | 2/2010 | Anglada | |
| 2010/0289772 | A1 | 11/2010 | Miller | |
| 2010/0302137 | A1 | 12/2010 | Benko | |
| 2011/0054360 | A1 | 3/2011 | Son | |
| 2011/0077486 | A1 * | 3/2011 | Watson | A61B 5/021 |
| | | | | 600/324 |
| 2011/0102378 | A1 | 5/2011 | Kim | |
| 2011/0148568 | A1 | 6/2011 | Lim | |
| 2012/0127070 | A1 | 5/2012 | Ryoo | |
| 2012/0157886 | A1 | 6/2012 | Tenn | |
| 2012/0188158 | A1 | 7/2012 | Tan | |
| 2012/0316456 | A1 * | 12/2012 | Rahman | G06F 1/163 |
| | | | | 600/547 |
| 2013/0265229 | A1 | 10/2013 | Forutanpour | |
| 2013/0289362 | A1 | 10/2013 | Kruglick | |
| 2013/0328761 | A1 | 12/2013 | Boulanger | |
| 2014/0003674 | A1 | 1/2014 | Coley | |
| 2014/0028546 | A1 | 1/2014 | Jeon | |
| 2014/0031698 | A1 | 1/2014 | Moon et al. | |
| 2014/0055352 | A1 | 2/2014 | Davis | |
| 2014/0139454 | A1 | 5/2014 | Mistry | |
| 2014/0155705 | A1 | 6/2014 | Papadopoulos | |
| 2014/0275852 | A1 | 9/2014 | Hong | |
| 2014/0334653 | A1 | 11/2014 | Luna | |
| 2015/0002391 | A1 | 1/2015 | Chia | |
| 2015/0009124 | A1 | 1/2015 | Antoniac | |
| 2015/0015481 | A1 | 1/2015 | Li | |
| 2015/0019135 | A1 | 1/2015 | Kacyvenski | |
| 2015/0022439 | A1 | 1/2015 | Alameh | |
| 2015/0031298 | A1 | 1/2015 | Holman | |
| 2015/0043770 | A1 | 2/2015 | Yen-Cherng | |
| 2015/0084860 | A1 | 3/2015 | Aleem | |
| 2015/0140934 | A1 | 5/2015 | Muhammad | |
| 2015/0168365 | A1 | 6/2015 | Connor | |
| 2015/0177836 | A1 | 6/2015 | Ouchi | |
| 2015/0182147 | A1 | 7/2015 | Sato | |
| 2015/0182160 | A1 | 7/2015 | Kim | |
| 2015/0370333 | A1 | 12/2015 | Ataee | |
| 2016/0091980 | A1 | 3/2016 | Baranski | |
| 2017/0031453 | A1 | 2/2017 | Presura | |

FOREIGN PATENT DOCUMENTS

| | | |
|---|---|---|
| WO | WO 2011/087890 | 7/2011 |
| WO | WO 2013/001265 | 1/2013 |
| WO | 2013/154864 | 10/2013 |
| WO | WO 2014/050298 | 4/2014 |
| WO | WO 2015/033327 | 3/2015 |
| WO | WO 2016/003268 | 1/2016 |

OTHER PUBLICATIONS

EP Communication pursuant to Rule 164(1) for Application No. 16740371.6-1972, dated Dec. 15, 2017.
Zhao et al., "Wireless Photoplethysmograph Knuckle Sensor System for Measuring Finger Motions", 2014 International Symposium on Optomechatronic Technologies, Nov. 5, 2014.
International Search Report and Written Opinion for Application No. PCT/KR2016/007100, dated Oct. 26, 2016.
U.S. Appl. No. 14/997,437, filed Jan. 15, 2016, Avila.
International Search Report and Written Opinion for Application No. PCT/KR2016/000525, dated Apr. 26, 2016.
Extended European Search Report for Application No. 16885201.0-1216, dated Dec. 20, 2018.
Non-Final Office Action for U.S. Appl. No. 14/997,437, dated Mar. 8, 2018.
Response to Non-Final Office Action for U.S. Appl. No. 14/997,437, dated Jun. 8, 2018.

* cited by examiner

Legend:
O Photodiode
X LED

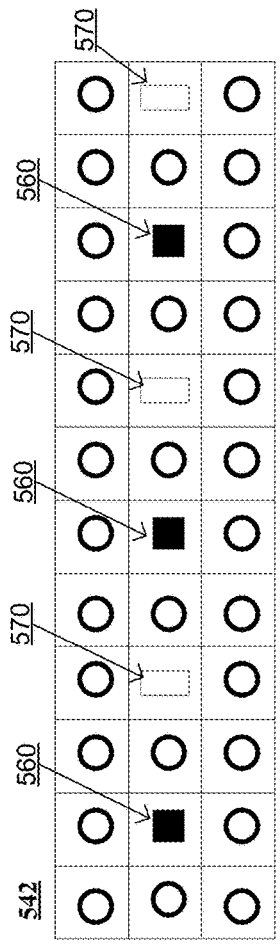
*FIG. 5E*
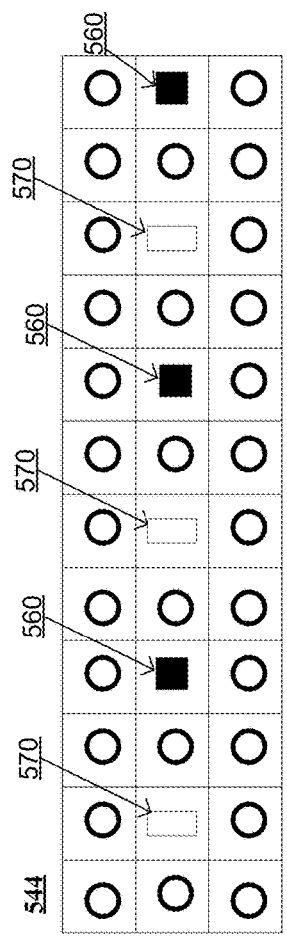
*FIG. 5F*
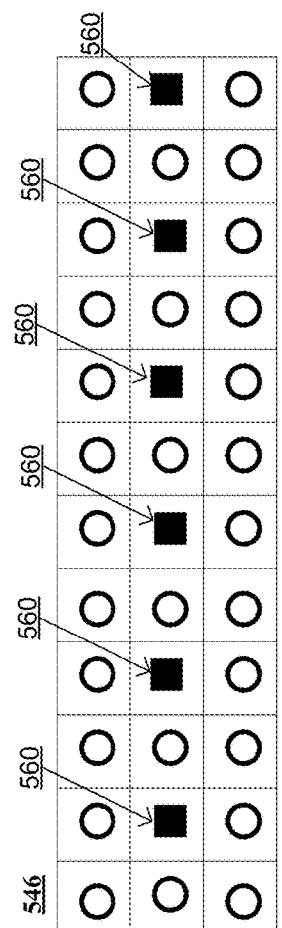
*FIG. 5G*
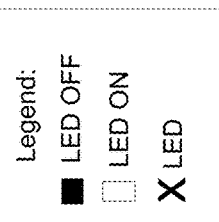

610

620

630

640

650

OPTICAL DETECTION AND ANALYSIS OF BONE

RELATED APPLICATION

This application claims the benefit, under 35 U.S.C. § 119(e), of U.S. Provisional Patent Application No. 62/105,163 filed 19 Jan. 2015, which is incorporated herein by reference.

TECHNICAL FIELD

This disclosure generally relates to improving usage and content for wearable electronic devices.

BACKGROUND

Mobile electronic devices provide a user with access to computing capabilities even as the user moves about various locations. Examples of mobile electronic devices include mobile phones, media players, laptops, tablets, personal digital assistants (PDAs), or hybrid devices that include functionality of multiple devices of this type.

Mobile electronic devices may be part of a communication network such as a local area network, wide area network, cellular network, the Internet, or any other suitable network. A mobile electronic device may use a communication network to communicate with other electronic devices, for example, to access remotely-stored data, access remote processing power, access remote displays, provide locally-stored data, provide local processing power, or provide access to local displays. For example, networks may provide communication paths and links to servers, which may host applications, content, and services that may be accessed or utilized by users via mobile electronic devices. The content may include text, video data, audio data, user settings or other types of data. Networks may use any suitable communication protocol or technology to facilitate communication between mobile electronic devices, such as, for example, BLUETOOTH, IEEE WI-FI (802.11a/b/g/n/ac), or Transmission Control Protocol/Internet Protocol (TCP/IP).

SUMMARY OF PARTICULAR EMBODIMENTS

In particular embodiments, a method may include outputting one or more sensor signals from an electronic device into a portion of a user's body, and detecting one or more deflected signals from the one or more sensor signals. The method may also include detecting a bone structure of the user's body based on the one or more deflected signals. Then, the method may include determining a user measurement based on the one or more deflected signals, the health measurement being adjusted by the detected bone structure.

In particular embodiments, an electronic device may include a light source configured to emit light that penetrates into a portion of a user's body, a plurality of light sensors configured to detect a pattern of diffusion of the emitted light, and a controller configured to detect a gesture made by the user based on the detected pattern of diffusion of the emitted light. The controller may then be configured to control the light source and the plurality of light sensors to detect the gesture made by the user.

The embodiments disclosed above are only examples, and the scope of this disclosure is not limited to them. Particular embodiments may include all, some, or none of the components, elements, features, functions, operations, or steps of the embodiments disclosed above. Embodiments according to the invention are in particular disclosed in the attached claims directed to a method, a storage medium, a system and a computer program product, wherein any feature mentioned in one claim category, e.g. method, can be claimed in another claim category, e.g. system, as well. The dependencies or references back in the attached claims are chosen for formal reasons only. However any subject matter resulting from a deliberate reference back to any previous claims (in particular multiple dependencies) can be claimed as well, so that any combination of claims and the features thereof are disclosed and can be claimed regardless of the dependencies chosen in the attached claims. The subject-matter which can be claimed comprises not only the combinations of features as set out in the attached claims but also any other combination of features in the claims, wherein each feature mentioned in the claims can be combined with any other feature or combination of other features in the claims. Furthermore, any of the embodiments and features described or depicted herein can be claimed in a separate claim and/or in any combination with any embodiment or feature described or depicted herein or with any of the features of the attached claims.

BRIEF DESCRIPTION OF THE DRAWINGS

FIGS. 5E-5G illustrate example diagrams of the operation of the light sources and light sensors of the optical detection device according to particular embodiments.

DESCRIPTION OF EXAMPLE EMBODIMENTS

System Overview

Figure 1:
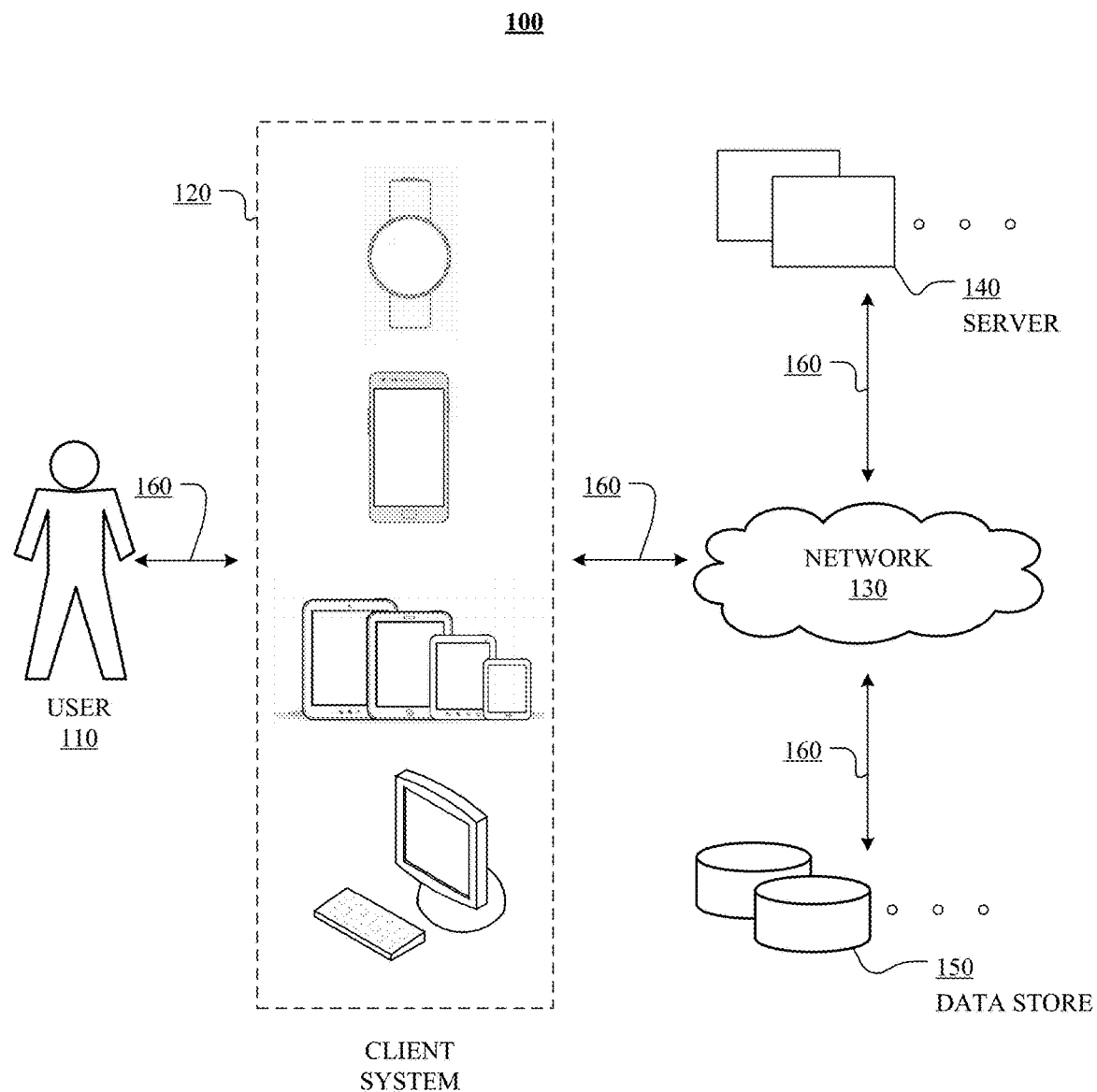
FIG. 1 illustrates an example network environment for particular embodiments of an optical detection system for internal body tissues and bone.

FIG. 1 illustrates an example network environment 100 for particular embodiments of an optical detection system for internal body tissues and bone. Network environment 100 includes a user 110, a client system 120, a network 130, one or more servers 140, and one or more data stores 150. User 110, client system 120, servers 140, and data stores 150 may be connected to each other by network 130 via links 160. Although FIG. 1 illustrates a particular arrangement of user 110, client system 120, network 130, servers 140, and data stores 150, this disclosure contemplates any suitable arrangement of user 110, client system 120, network 130, servers 140, and data stores 150. As an example and not by way of limitation, two or more of client system 120, servers 140, and data stores 150 may be connected to each other directly, bypassing network 130. As another example, two or more of client system 120, servers 140, and data stores 150 may be physically or logically co-located with each other in whole or in part. Moreover, although FIG. 1 illustrates a particular number of user 110, client system 120, network 130, servers 140, and data stores 150, this disclosure contemplates any suitable number of user 110, client system 120, network 130, servers 140, and data stores 150. As an example and not by way of limitation, network environment 100 may include multiple users 110, client systems 120, networks 130, servers 140, and data stores 150.

In particular embodiments, user 110 may be an individual (e.g., human user), an entity (e.g., an enterprise, business, or third-party application), or a group (e.g., of individuals or entities) that interacts or communicates with client system 120. In particular embodiments, client system 120 may be any suitable computing device, such as, for example, a wearable computing device, a mobile computing device, a smartphone, a cellular telephone, a tablet computer, a laptop computer, a personal computer, an augmented/virtual reality device, or any combination thereof. User 110 may interact with one or more of these devices. In addition, these devices may communicate with each other via network 130, directly (e.g., by non-network connections), by any other suitable methods, or any combination thereof. As an example and not by way of limitation, the devices of client system 120 may communicate with network 130 via a wireless communications protocol, such as Wi-Fi or BLUETOOTH. In particular embodiments, client system 120 may include a web browser, such as MICROSOFT INTERNET EXPLORER, GOOGLE CHROME or MOZILLA FIREFOX, and may have one or more add-ons, plug-ins, or other extensions, such as TOOLBAR or YAHOO TOOLBAR. A user at client system 120 may enter a Uniform Resource Locator (URL) or other address directing the web browser to a particular server (such as server 140), and the web browser may generate a Hyper Text Transfer Protocol (HTTP) request and communicate the HTTP request to server. The server may accept the HTTP request and communicate to client system 120 one or more Hyper Text Markup Language (HTML) files responsive to the HTTP request. Client system 120 may render a webpage based on the HTML files from the server for presentation to the user. This disclosure contemplates any suitable webpage files. As an example and not by way of limitation, webpages may render from HTML files, Extensible Hyper Text Markup Language (XHTML) files, or Extensible Markup Language (XML) files, according to particular needs. Such pages may also execute scripts such as, for example and without limitation, those written in JAVASCRIPT, JAVA, MICROSOFT SILVERLIGHT, combinations of markup language and scripts such as AJAX (Asynchronous JAVASCRIPT and XML), and the like. Herein, reference to a webpage encompasses one or more corresponding webpage files (which a browser may use to render the webpage) and vice versa, where appropriate.

In particular embodiments, network 130 may be any suitable network. As an example and not by way of limitation, one or more portions of network 130 may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or a combination of two or more of these. Network 130 may include one or more networks.

In particular embodiments, links 160 may connect client system 120, servers 140, and data stores 150 to network 130 or to each other. This disclosure contemplates any suitable links 160. In particular embodiments, one or more links 160 include one or more wireline (such as for example Digital Subscriber Line (DSL) or Data Over Cable Service Interface Specification (DOCSIS)), wireless (such as for example Wi-Fi or Worldwide Interoperability for Microwave Access (WiMAX)), or optical (such as for example Synchronous Optical Network (SONET) or Synchronous Digital Hierarchy (SDH)) links. In particular embodiments, one or more links 160 each include an ad hoc network, an intranet, an extranet, a VPN, a LAN, a WLAN, a WAN, a WWAN, a MAN, a portion of the Internet, a portion of the PSTN, a cellular technology-based network, a satellite communications technology-based network, another link 160, or a combination of two or more such links 160. Links 160 need not necessarily be the same throughout network environment 100. One or more first links 160 may differ in one or more respects from one or more second links 160.

In particular embodiments, servers 140 may be any suitable servers. Each server 140 may be a unitary server or a distributed server spanning multiple computers or multiple datacenters. Servers 140 may be of various types, such as, for example and without limitation, web server, file server, application server, exchange server, database server, proxy server, another server suitable for performing functions or processes described herein, or any combination thereof. In particular embodiments, each server 140 may include hardware, software, or embedded logic components or a combination of two or more such components for carrying out the appropriate functionalities implemented or supported by server 140.

In particular embodiments, data stores 150 may be any suitable data stores. Data stores 150 may be used to store various types of information. In particular embodiments, the information stored in data stores 150 may be organized according to specific data structures. In particular embodiments, each data store 150 may be a relational, columnar, correlation, or other suitable database. Data store 150 may include networked storage such as cloud storage or other network accessible storage. Additionally or alternatively, data store 150 may include local storage within or directly attached to any of the devices of client system 120, such as solid state drives ("SSDs") or hard disk drives ("HDDs").

In particular embodiments, data store 150 may store various data structures relevant to an optical detection device and the processing of data collected by the optical detection device. As an example and not by way of limitation, data store 150 may store a data structure corresponding to biometrics information (e.g., cross sections and measurements of tendons, muscles, bones, and other body tissue). As another example and not by way of limitation, data store 150 may store a data structure corresponding to gesture sensor data and pre-classification calibration data collected by sensors of the optical detection device. As yet another example and not by way of limitation, data store 150 may store a data structure corresponding to features data and features vectors determined based on a features evaluation process for the optical detection device. As yet another example and not by way of limitation, data store 150 may store a data structure corresponding to classification data used for classifying user gesture data. As yet another example and not by way of limitation, data store 150 may store a data structure corresponding to calibration measurements, bone structure measurements, calibration parameters, frame of reference data, and tendon characteristics data associated with a gesture recognition process. As yet another example and not by way of limitation, data store 150 may store a data structure corresponding to calibration data and classification algorithms for a slippage correction process. As yet another example and not by way of limitation, data store 150 may store a data structure corresponding to classification algorithms, user biometric characteristics, and user-specific "fingerprint" data for a biometric authentication process. As yet another example and not by way of limitation, data store 150 may store a data structure corresponding to classification algorithms, clusters of user profile characteristics, and user-profile "fingerprint" data for a profile identification process. Although this disclosure describes or illustrates particular types of components and uses of these component of network environment 100, this disclosure contemplates any suitable types of components, any suitable network topology (e.g., including a standalone-device topology), and any suitable uses for these components of network environment 100.

DESCRIPTION OF EXAMPLE EMBODIMENTS

The global wearable device market is a rapidly-growing market as wearable technology becomes an integral part of the Internet of Things in which a network of physical objects/things embedded with electronics, software, sensors, and network connectivity enables these objects/things to communicate with one another and collect and exchange data with one another. As the technology quickly evolves in this area, users need to be able to seamlessly control wearable devices and nearby computing devices through wearable devices. Example considerations for a number of wearable devices include the ability of the device to be seamless worn on the user's body without being too large or obtrusive while being used in everyday situations without discomfort, annoyance, or embarrassment; be always available and easily accessible at all times and in all situations; to be intuitive to use, including using simple, natural, and non-fatigue-inducing gestures and/or movements that can be hands-free in operation; be easily integrate into existing devices such as watches (e.g., smartwatches) and other accessories (e.g., wristbands, bracelets, rings, armbands, etc.); and be efficient in power consumption.

In particular embodiments, a wearable device may detect one or more user gestures performed with or on the device. Gestures may be of any suitable type, may be detected by any suitable sensors (e.g. inertial sensors, touch sensors, cameras, or depth sensors), and may be associated with any suitable functionality. As an example, a user gesture may include a predetermined amount of movement or sequence of movements of the user associated with a portion of the user's body (e.g., the movement of a user's fingers, as discussed below). When appropriate, sensors used to detect gestures (or processing used to initiate functionality associated with a gesture) may be activated or deactivated to conserve power or provide security. In particular embodiments, gestures may include gestures that involve at least one hand of the user and an appendage on which the device is worn (e.g., the wrist of the hand, or alternatively, the wrist of the other hand). For example, in particular embodiments, a user may use the hand/arm on which the device is worn to sense a gesture of that particular hand/arm. Alternatively, a user may use the hand/arm on which the device is worn to appropriately aim an optical sensor of the device and may move or position the other arm/hand/fingers to perform a particular gesture. More information on gestures, gesture processing, and examples of gestures may be found in U.S. patent Ser. No. 14/015,795, filed on 30 Aug. 2013 and published as U.S. Patent Application Publication No. 2014/0139637, which is incorporated by reference.

In particular embodiments, a wearable device may include sensing technology for gesture recognition that utilizes light in the visible and/or invisible spectrum to detect changes in the position and form of body tissue (e.g., tendons, muscles, etc.) and bone. The wearable device may include a light source (e.g., a light-emitting diode) and a light sensor (e.g., a photodiode) that are arranged to face toward the skin of the user when worn on the user's body.

In operation, the light source may emit light in the visible and/or invisible spectrum into the underlying tissue of the user. A portion of the emitted light backward scatters as a result of being reflected by the underlying tissue. Additionally, a portion of the emitted light forward scatters after penetrating into the underlying tissue of the user's body and being deflected by the underlying tissue. Reflected light may include backward-scattered light, and deflected light may include both backward-scattered light and forward-scattered light. In such a manner, backward scattered light corresponds to light that is deflected in a direction no more than −90° of the direction of propagation of the emitted light wave or in a direction no more than 90° of the direction of propagation of the emitted light wave, and forward scattered light corresponds to light that is deflected in a direction that is within −90° and −180° of the direction of propagation of the emitted light wave or within 90° and 180° of the direction of propagation of the emitted light wave.

In an example embodiment, the wearable device includes multiple light sources and/or multiple light sensors. The light sources may be configured into different configurations (e.g., clustered, symmetric, etc.) and the light sensors may be positioned at different distances from each other to obtain different light penetration at different depths. This configuration of light sources and light sensors, in addition to the measuring of the backward and forward scattering of light, facilitates measuring different spatial patterns of diffusion that can be processed to obtain data on the position and form of body tissue and bone. These optical characteristics of spatial patterns of diffusion, together with the characteristics of the underlying internal body tissue, can then be used to identify user inputs (e.g., a gesture made by the user).

In particular embodiments, wearable devices may be configured to perform measurements on the user's body. For example, a wearable device may utilize a light source and a light sensor to perform measurements of the user's body. These measurements may be used to measure the health of the user, monitor activities of the user, detect gestures as user input, other relevant measurements or statistics, or any combination there. These measurements may be sensitive to the location of the wearable device on the user's body. For example, a slight shift in the location of the wearable device around a target area of the user's body may significantly affect the measurements collected by the wearable device. In addition, the target area for the wearable device may be variable because each user may wear the wearable device slightly differently, the wearable device may be at a different location each time the user puts on the wearable device, and during operation the wearable device may shift in location. In addition, the wearable device may need to be calibrated for each user based on the particular characteristics of the user (e.g., prior to being used to perform gesture recognition, the device may need to be calibrated based on user-specific characteristics, as described above, and described in more detail below). For example, the calibration process may include performing a number of predefined gestures in a fast and efficient manner while correcting for error. This calibration may be based on a fixed frame of reference (e.g., one or more bones of the user), which can facilitate localizing the device with respect to the user's body (e.g., specific portions of the user's body, such as a particular bone or combination of bones), normalizing measurement data, and facilitating device calibration. These calibrated measurements of the wearable devices may be used to correct for slippage of the wearable device in order to increase its operational accuracy for gesture recognition and biosensing applications (e.g., biometric measurements, healthcare applications, virtual reality applications, etc.), in addition to performing tissue and bone characteristics analysis (e.g., size, density, composition, etc.) for use in biometric authentication and profile identification.

Figure 2A:
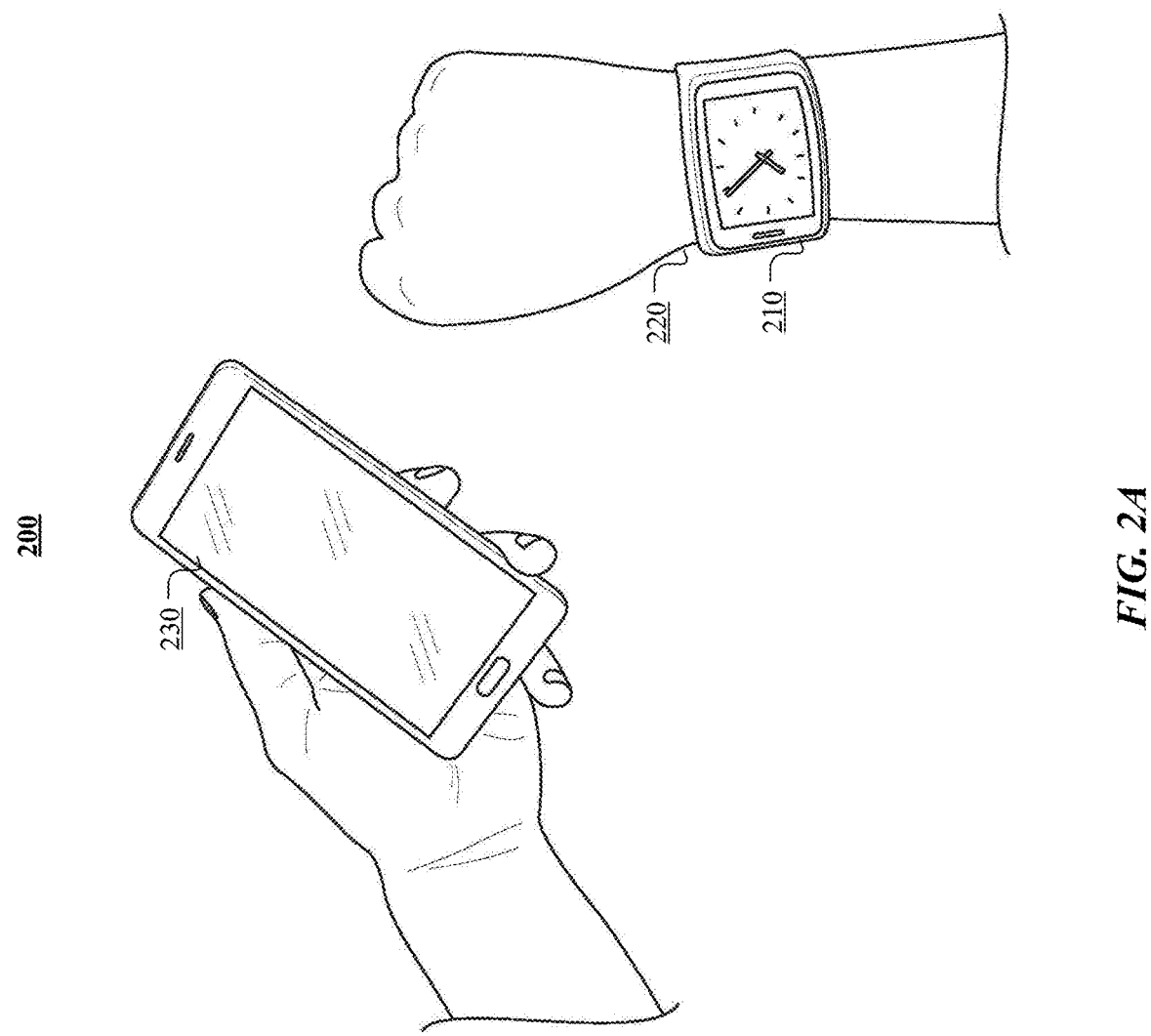
FIG. 2A illustrates an example optical detection system according to particular embodiments of the invention.
Figure 2B:
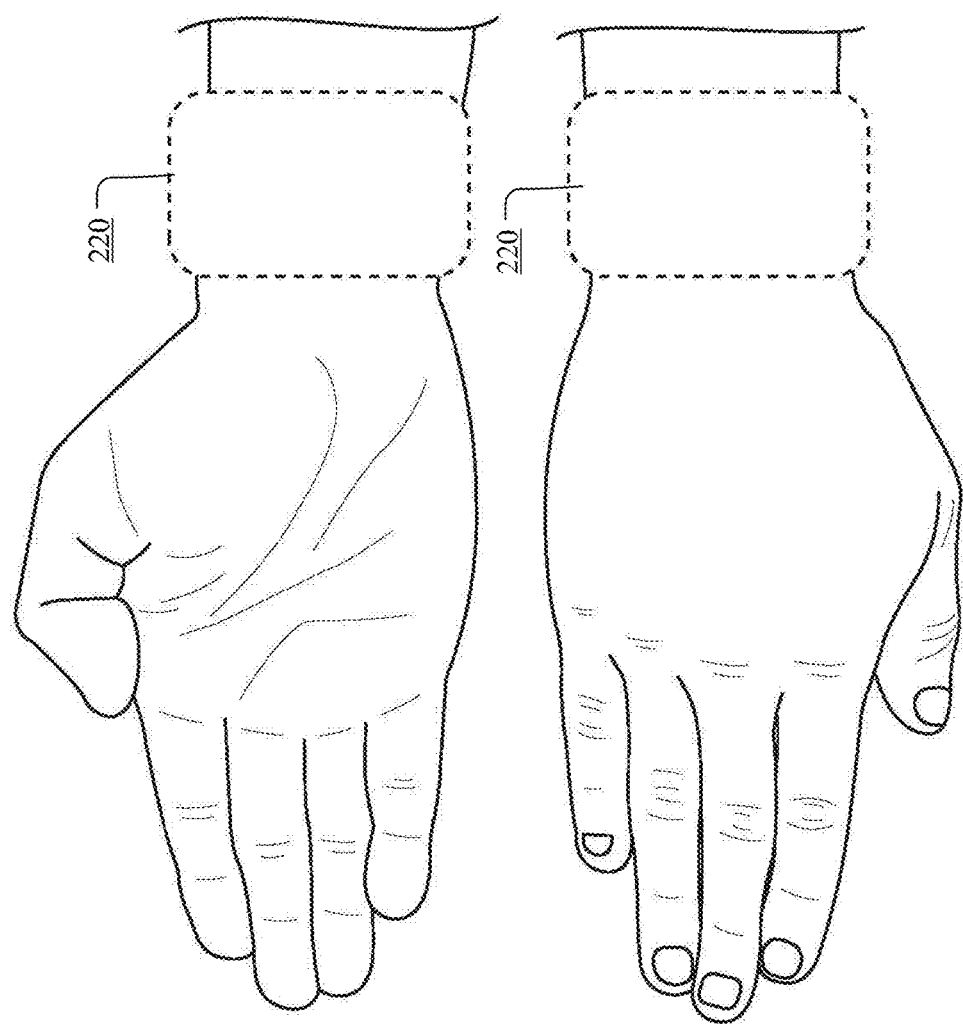
FIG. 2B illustrates example positioning information for the optical detection system according to particular embodiments of the invention.

FIG. 2A illustrates an example optical detection system 200 according to particular embodiments. FIG. 2B illustrates example positioning information for the optical detection system 210 according to particular embodiments. In particular embodiments, as shown in FIG. 2A, optical detection system 200 may include an optical detection device 210. Optical detection device 210 may be a wearable electronic device (e.g., a client device 120) that can be worn by user 110 on a portion of his/her body, such as an arm, wrist, finger, leg, ankle, toe, torso, neck, head, any other suitable portion of the body, or any combination thereof. As an example and not by way of limitation, a wearable device worn on a user's wrist may be configured to detect hand and finger gestures, a wearable device worn on a user's ankle may be configured to detect foot and toe gestures, a wearable device worn on a user's neck may be configured to detect head gestures, and a wearable device worn on a user's torso (e.g., chest area, stomach area, etc.) may be configured to detect arm, hand, leg, or foot gestures. In particular embodiments, as shown in FIG. 2B, optical detection device 210 may be a smartwatch-like device worn on body 220 (e.g., a wrist portion) of user 110. In other particular embodiments, optical detection device may be a sock-like or shoe-like device worn on body (e.g., an ankle and/or a foot portion) of user 110. In other particular embodiments, optical detection device may be a necklace-like device worn on body (e.g., a neck portion) of user 110. In other particular embodiments, optical detection device may be a band or electronic fabric (e.g., shirt) worn on body (e.g., torso portion) of user 110. As an example and not by way of limitation, data that may be collected at the wrist portion of body 220, ankle portion of the body, neck portion of the body and torso portion of the body includes body tissue characteristics of bones (e.g., ulna, radius, etc.), tendons (e.g., flexor tendons, extensor tendons, etc.), ligaments (e.g., ulnar collateral ligament, transverse carpal ligament, radial collateral ligament, etc.), and muscles (e.g., muscles connected to the flexor tendons, muscles connected to the extensor tendons, etc.), and blood vessels (e.g., radial artery, ulnar artery, etc.), including changes in their location, size, density, composition, other relevant measurements, or any combination thereof. In particular embodiments, optical detection system 200 may include additional components such as a data store (e.g., similar to data store 150 but part of optical detection system 200), any of the other devices of client system 120, other relevant components, or any combination thereof. Although this disclosure describes an optical detection system 200 in a particular manner, this disclosure contemplates an optical detection system 200 in any suitable manner and with any suitable components.

In particular embodiments, as shown in FIG. 2A, optical detection system 200 may include a mobile electronic device 230. Optical detection device 210 may connect to mobile electronic device 230 directly or via network 130, which may facilitate interaction between and/or transfer of data between optical detection device 210 and mobile electronic device 230. In particular embodiments, mobile electronic device 230 may be a smartphone-like device. Optical detection device 210 and mobile electronic device 230 may be connected to network 130, servers 140, data stores 150, or any combination thereof. Data (e.g., bone and/or tissue characteristics data, spatial patterns of diffusion of light, device location data, etc.) may be stored on optical detection device 210, mobile electronic device 230, other client systems 120, data stores 150, other suitable databases, or any combination thereof. In addition, the processing of the data and computations of particular algorithms and calibration techniques (as discussed below) may be performed by optical detection device 210, mobile electronic device 230, on servers 140, by any other client system 120, other suitable devices/systems, or any combination thereof. In particular embodiments, the processing of the data and computations of particular algorithms may be performed by accessing user data, frame of reference data, calibration data, other relevant data, or any combination thereof, from data stores 150 via network 130.

Figure 3A:
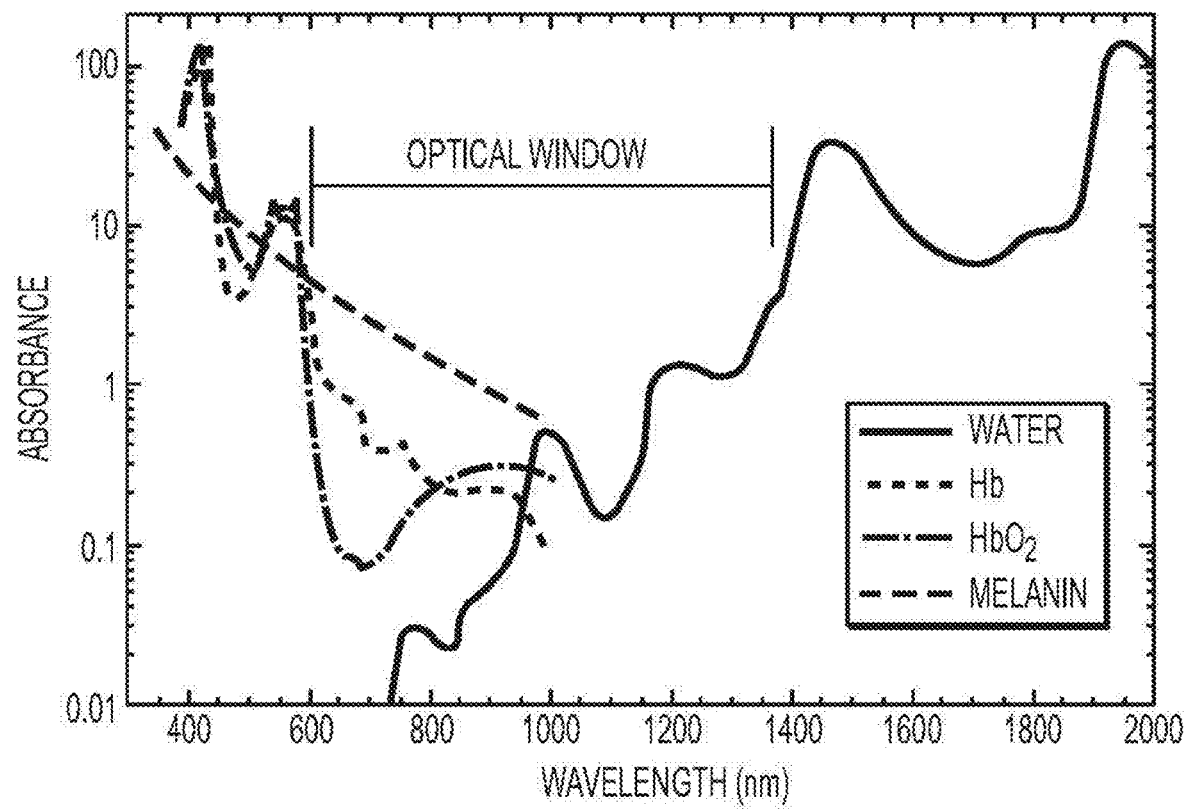
FIG. 3A illustrates an example optical window for body tissue according to particular embodiments of the invention.
Figure 3B:
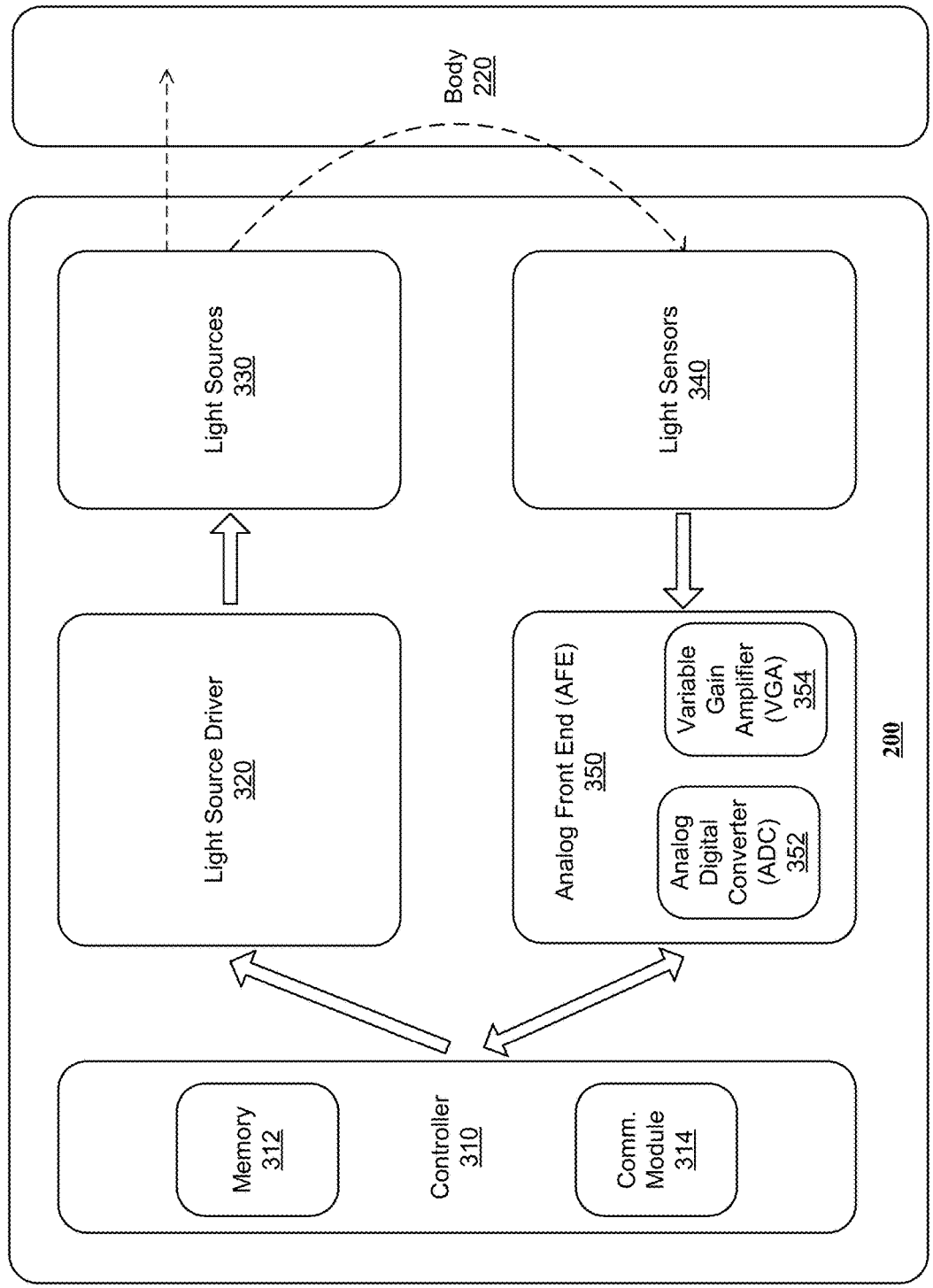
FIG. 3B illustrates a diagram of example components of an optical detection device according to particular embodiments of the invention.
Figure 3C:
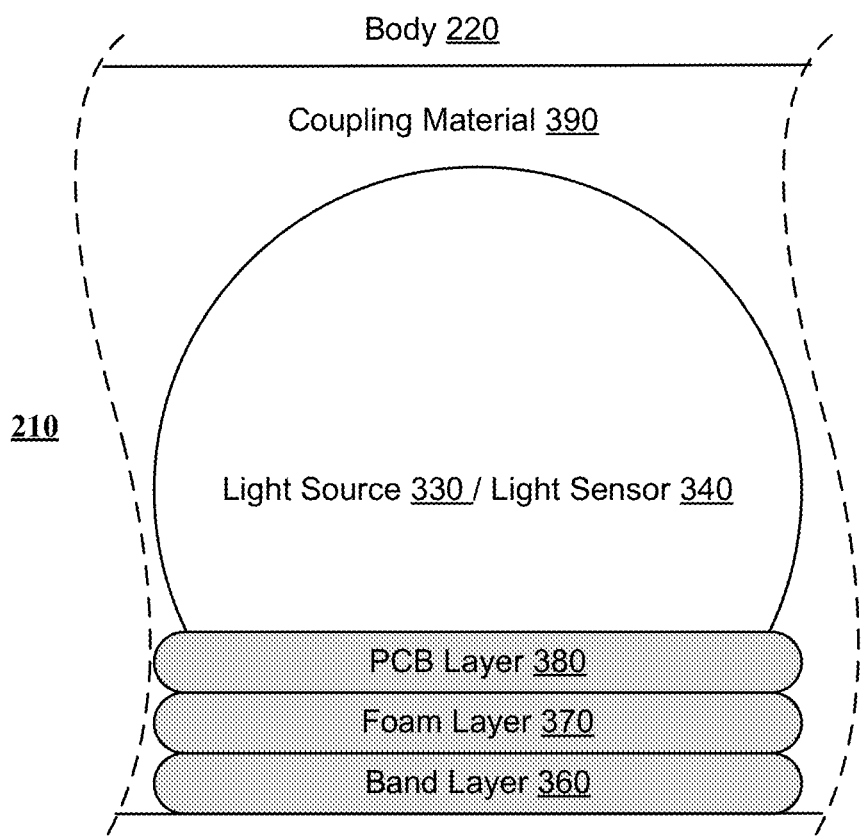
FIG. 3C illustrates a cross-section of optical detection device according to particular embodiments of the invention.

FIG. 3A illustrates an example optical window for body tissue according to particular embodiments, FIG. 3B illustrates a diagram of example components of optical detection device 210 according to particular embodiments illustrates, and FIG. 3C illustrates a cross-section of optical detection device 210 according to particular embodiments. As shown in FIG. 3B, optical detection device 210 may include a controller 310, a light source driver 320, light sources 330, light sensors 340, and an analog front end (AFE) 350. Controller 310 may directly or indirectly control light source driver 320, light sources 330, light sensors 340, and AFE 350. Controller 310 may include a memory 312 that stores software instructions executable by controller 310. As an example and not by way of limitation, the instructions may be implemented by controller 310 to control light source driver 320, light sources 330, light sensors 340, AFE 350, or any combination thereof. Controller 310 may also include a communication module 314 that is configured to transmit information (e.g., a detected gesture, an action associated with the detected gesture, other relevant information, or any combination thereof, as discussed below) made by the user to a second device. The second device may include mobile electronic device 230, as shown in FIG. 2A. In particular embodiments, communication module 314 may communicate and transmit information with mobile electronic device 230 over network 130 via an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, any other suitable connections, or any combination thereof.

In particular embodiments, the emitting hardware may include light source driver 320 and light sources 330. Light source driver 320 may include a programmable electrical current source, and may be configured to direct power to light sources 330 based on instructions from controller 310. Light sources 330 may include one or more light-emitting diodes (LEDs) that emit colored and/or colorless light. As example and not by way of limitation, LEDs of light sources 330 may emit near infrared (NIR) light, infrared (IR) light, visible light (e.g., red light, white light, blue light, other colored light, etc.), ultraviolet (UV light), other suitable light, or any combination thereof. In particular embodiments, controller 310 may control light source driver 320 to drive the LEDs of light sources 330 to emit light onto the user's body 220 (e.g., onto a wrist portion). The sensing hardware may include light sensors 340 and AFE 350. Light sensors 340 may include one or more photodiodes that are configured to detect light and then convert the light into current that is then sent to AFE 350 for processing. AFE 350 may be include a set of analog signal conditioning circuitry that interfaces with controller 310, an analog digital converter (ADC) 352, and a variable gain amplifier (VGA) 354. VGA 354 may be configured to vary its gain controllable by the current running through light sources 330 depending on a control voltage determined by controller 310 in order to increase or decrease an attenuation value, and ADC 352 may be configured to convert the voltage received from light sensors 340 to digital numbers that represents the quantity's amplitude, which can then be plotted against time over a predetermined period of time to produce graphs of signals received for particular gestures (as discussed below in conjunction with FIGS. 6A-6E).

In particular embodiments, the light emitted by light sources 330 may include near-infrared light (NIR), which may be emitted and sensed by the LEDs and photodiodes, respectively, to detect bone and other body tissue characteristics. As shown in FIG. 3A, NIR has substantial depth penetration in body tissue from 650 nm to 1400 nm wavelengths, which is the range for the NIR optical window for body tissue, with 850 nm wavelength being especially penetrative. In this region, the absorbance of light by water, melanin, oxygen-hemoglobin (HbO$_2$), and deoxy-hemoglobin (Hb) is low and allows for better imaging of the body tissue. In addition, because bone and other body tissue have different compositions and structures, NIR light at these wavelengths behaves differently and results in differentiable distinctions between bone and other body tissue.

In example embodiments, the light source 330 is configured to generate light within an optical window of about 650 nm to 1400 nm wavelengths. In another example embodiment, the light source 330 is configured to generate light within an optical window of about 750 nm to 950 nm wavelengths. In another example embodiment, the light source 330 is configured to generate light at about 850 nm wavelength. In particular embodiments, a plurality of wavelengths within the optical window are used to generate the spatial patterns of diffusion of light, as discussed in more detail below.

In particular embodiments, optical detection device 310 may comprise a structure as show in FIG. 3C, which improves the effectiveness of optical detection device 210 by improving the transmission of light and the contact between the body 220 of the user and the LEDs of light sources 330 and/or photodiodes of light sensor 340. In particular embodiments, optical detection device 310 may include a band layer 360, a foam layer 370, a printed circuit board (PCB) layer 380, and coupling material 390. Band layer 360 (e.g., a wristband layer) may comprise a layer of material that controller 310, memory 312, light source driver 320, and AFE 350 are attached to. Foam layer 370 may be disposed above band layer 360, and may help make the band layer 360 less rigid and more adaptable to irregular surfaces produced by body tissue and bone. PCB layer 380 may be disposed above foam layer 370 and may help to mechanically support and electrically connect electronic components. As an example and not by way of limitation, PCB layer 380 may electronically connect controller 310, light source driver 320, and AFE 350 with light sources 330 and light sensors 340. A layer of light sources 330 and light sensors 340 is disposed above PCB layer 380. In addition, coupling material 390 may be disposed above PCB layer 380 and may surround the layer of light sources 330 and light sensors 340. Coupling material 390 may be disposed against body 220 when optical detection device 310 is worn by user 110, and may help in facilitating transmission of light between the layer of light sources 330 and light sensors 340 and body tissue of body 220 by allowing for the transmission of light with minimal absorption, attenuation or disturbance.

Figure 4A:
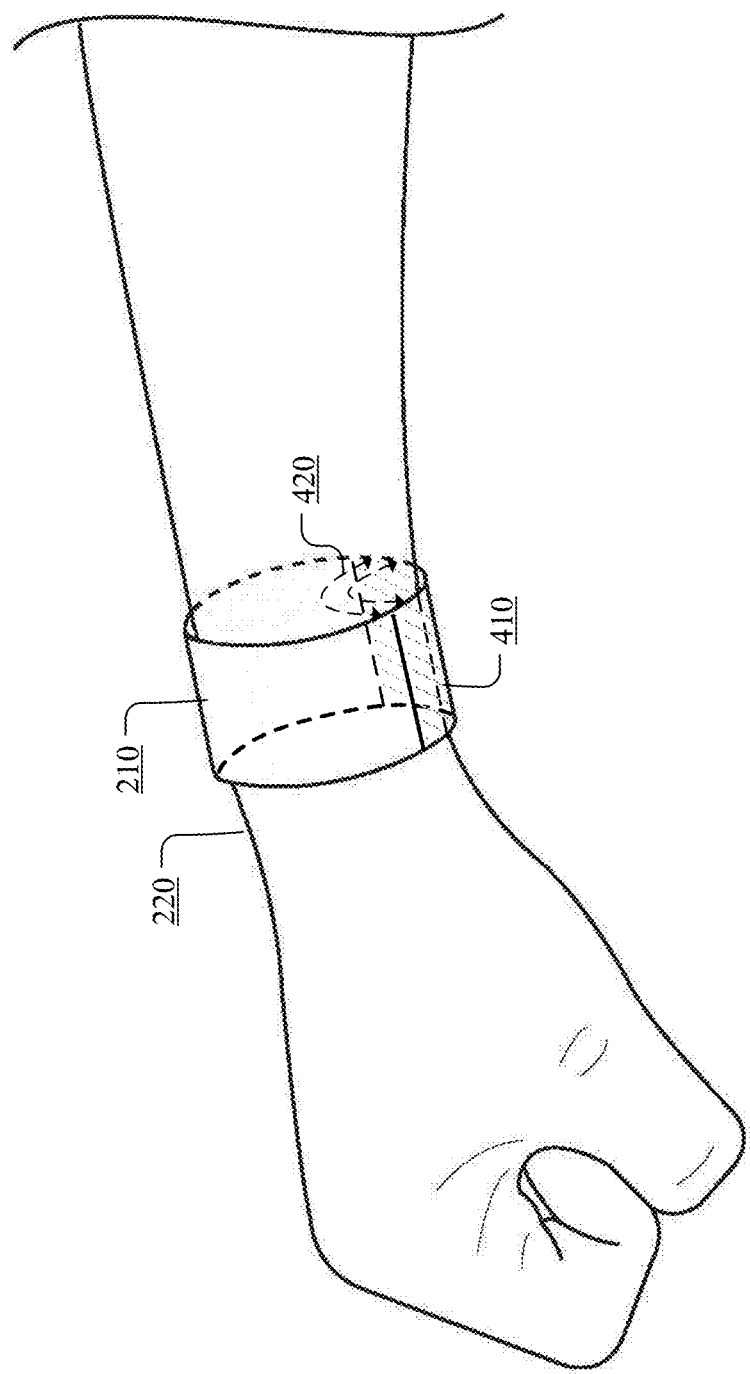
FIG. 4A illustrates an example embodiment of an optical detection device that includes a configuration of light sources and light sensors that covers a portion of a user's body according to particular embodiments of the invention.
Figures 4B, 4C:
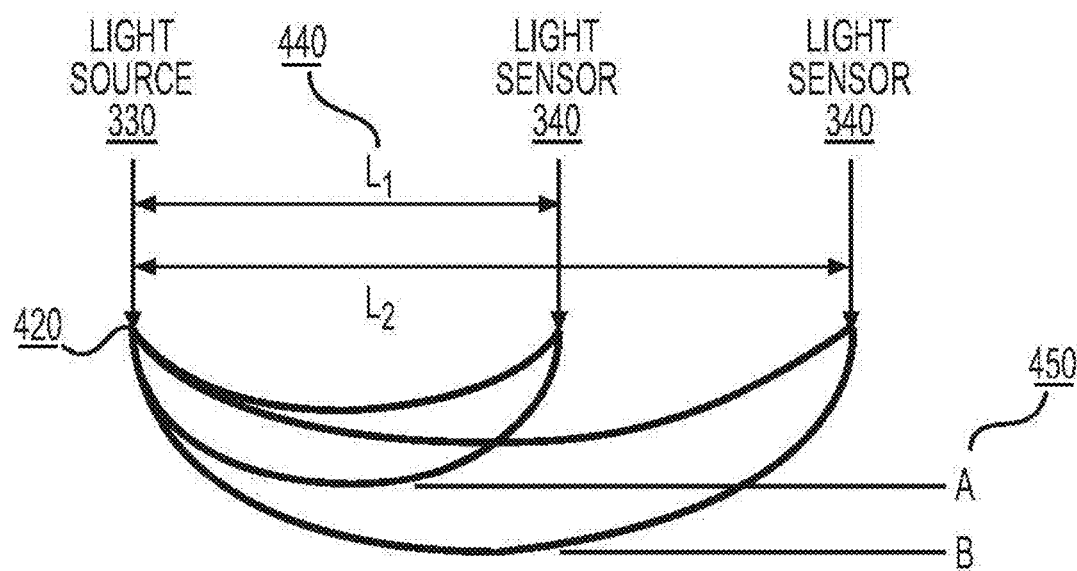
FIG. 4B illustrates an example diagram of a configuration of light sources and light sensors of the optical detection device according to particular embodiments of the invention.
FIG. 4C illustrates the depth penetration of light during backwards scattering of light according to particular embodiments of the invention.

FIG. 4A illustrates an example embodiment of optical detection device 210 that includes a configuration of light sources and light sensors that covers a portion of a user's body according to particular embodiments, FIG. 4B illustrates an example diagram of the configuration of light sources 330 and light sensors 340 according to this embodiment, and FIG. 4C illustrates the depth penetration of light during backwards scattering of light according to this embodiment. In particular embodiments, an optical detection device 210 worn on a user's wrist may include a wristband housing a configuration of light sources 330 and light sensors 340. As shown in FIG. 4A, optical detection device 210 may include a configuration 410 of light sources 330 and light sensors 340 that covers a portion of a wrist of user body 220. Configuration 410 may be located at any position around the wrist of user body 220 such that configuration 410 covers a portion of the wrist. As an example and not by way of limitation, the configuration 410 may be located adjacent to a bottom portion of the wrist of user body 220 (e.g., as shown in FIG. 4A), adjacent to a top portion of the wrist of user body 220, adjacent to a side portion of the wrist of user body 220, or any other suitable portion of the wrist of user body 220. In particular embodiments, light 420 may be emitted by light sources 330 and then detected by light sensors 340, as discussed below. In particular embodiments, light sources 330 may include red LEDs. As an example and not by way of limitation, as shown in FIG. 4B, a matrix 430 of light sources 330 and light sensors 340 may include a total of twenty four (24) light sources 330 (e.g., LEDs) and twenty four (24) light sensors 340 (e.g., photodiodes) distributed in an eight by six (8×6) grid. In particular embodiments, the light sources 330 and light sensors 340 are organized in an alternating LED-photodiode configuration. In particular embodiments, as shown in FIG. 4A, when controller 310 controls light sources 330 to emit light 420 that penetrates into the body tissue of the user, depending on the wavelength of the light (e.g., see FIG. 3A), some of light 420 may be absorbed by the body tissue while some of light 420 will be deflected by certain body tissue or bone. In particular embodiments, the depth of penetration of light 420, and the corresponding imaging location, may be determined by the distance between a light source 330 and a light sensor 340, the wavelength(s) of light being outputted by light source 330, the number and/or configuration of light source 330 and light sensor 340, other relevant features, and any combination thereof.

As shown in FIG. 4C, a distance 440 between light source 330 and light sensor 340 determines a penetration depth 450. When distance 440 between light source 330 and light sensor 340 is L1, penetration depth 450 of light 420 is at a depth of A, whereas when distance 440 between light source 330 and light sensor 340 is L2, which is longer than L1, penetration depth 450 of light 420 is at a depth of B, which is deeper than A. In addition, as shown in FIG. 1, light 420 emitted by light sources 330 may pass through the body tissue before it is scattered back to be detected by light sensors 430 following a substantially curved path (e.g., a banana-shaped path). In particular embodiments, the backward-scattered light 420 may include light that is emitted by light sources 330 at a first portion of optical detection device 210 that is deflected by body tissue and/or bone in a direction no more than −90° of the direction of propagation of the emitted light wave or in a direction no more than 90° of the direction of propagation of the emitted light wave.

Alternatively, in particular embodiments, the wristband housing may include the configuration of light sources 330 and lights sensors 340 that covers a wrist area (e.g., covers an entire area surrounding the wrist). As an example and not by way of limitation, the configuration of light sources 330 and light sensors 340 may be disposed along the entire length of the wristband housing. As another example and not by way of limitation, the configuration may include one or more first light sources 330/light sensors 340 configurations at a first portion of the wristband housing (e.g., at a top portion of the wrist) and one or more second light sources 330/light sensors 340 configurations at a second portion of the wristband housing (e.g., at a bottom portion of the wrist opposite of the top portion), and one or more spaces between the first light sources 330/light sensors 340 configuration and second light sources 330/light sensors 340 configuration.

Figure 5A:
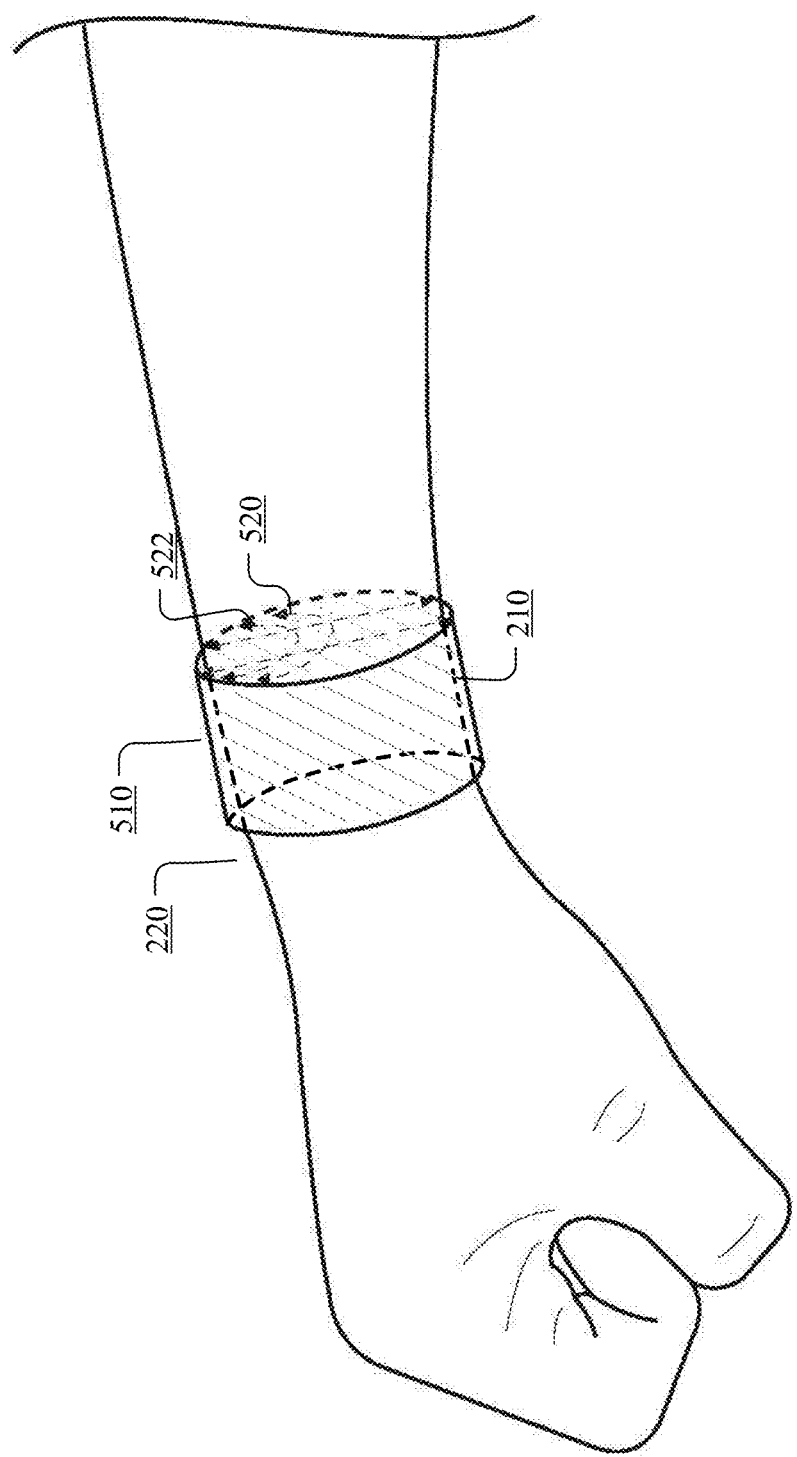
FIG. 5A illustrates an example embodiment of an optical detection device that includes a configuration of light sources and light sensors that covers an entire portion of a user's body.
Figures 5B, 5C, 5D:
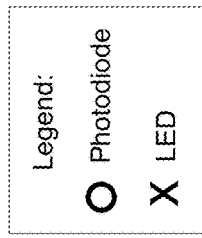
FIGS. 5B-5D illustrate example diagrams of the configuration of light sources and light sensors of the optical detection device according to particular embodiments.

FIG. 5A illustrates an example embodiment of optical detection device 210 that includes a configuration of light sources 330 and light sensors 340 that covers a portion of a user's body according to particular embodiments, FIGS. 5B-5D illustrate example diagrams of the configuration of light sources 330 and light sensors 340 according to this embodiment, and FIGS. 5E-5G illustrate example diagrams of the operation of the light sources 330 and light sensors 340 according to this embodiment. As shown in FIG. 5A, optical detection device 210 may include a configuration 510 of light sources 330 and light sensors 340 that spans the entire portion of the wrist of user body 220. In particular embodiments, the light sources 330 may comprise NIR LEDs, and light sensors 340 may comprise photodiodes configured to detect the NIR light. As an example and not by way of limitation, shown in FIG. 5B, a matrix 530 of light sources 330 and light sensors 340 may include a total of eighteen (18) light sources 330 (e.g., NIR LEDs) and eighteen (18) light sensors 340 (e.g., photodiodes) distributed in a twelve by three (12×3) grid. In particular embodiments, the light sources 330 and light sensors 340 may be organized in a symmetric, alternating LED-photodiode configuration. Alternatively, in particular embodiments, a matrix 540 of light sources 330 and light sensors 340 may include a total of six (6) light sources 330 (e.g., NIR LEDs) and thirty (30) light sensors 340 (e.g., photodiodes) distributed in a twelve by three (12×3) grid. The light sources 330 and light sensors 340 may be organized into clusters such that only the middle row includes an alternating LED-photodiode configuration while the top row and bottom row include only photodiodes. Alternatively, in particular embodiments, a matrix 550 of light sources 330 and light sensors 340 may include a total of thirty (30) light sources 330 (e.g., NIR LEDs) and six (60) light sensors 340 (e.g., photodiodes) distributed in a twelve by three (12×3) grid. The light sources 330 and light sensors 340 may be organized into clusters such that only the middle row includes an alternating LED-photodiode configuration while the top row and bottom row include only LEDs. Among these three configurations, matrix 540 may be the most energy-efficient configuration due to having the least number of LEDs, while matrix 550 may be the most energy-consuming configuration due to having the most number of LEDs. Matrix 530 may be a moderately energy-consuming configuration due to equal numbers of LEDs to photodiodes. Matrix 550 may be best suited to detect forward-scattered light because it provides the most emitted light (needed to penetrate through the body). Matrix 540 may produce the necessary emitted light to detect backward-scattered light (being less than the amount of emitted light needed to detect forward-scattered light). Matrix 530 may be an intermediate solution to detect forward-scattered light as well as backward-scattered light.

In particular embodiments, when light sources 330 are emitting light, light sources 330 may be configured to cycle through different configurations. As an example and not by way of limitation, as shown in FIGS. 5E-5G, the six light sources 330 may be operated based on different patterns. In a first configuration 542, controller 310 may be configured to power off LEDs 560 while powering on LEDs 570. In a second configuration 544, controller 310 may be configured to power on LEDs 570 while powering off LEDs 560. In a third configuration 546, controller 310 may be configured to power off all LEDs 560. In particular embodiments, light sources 330 may be configured to cycle through a combination of the first configuration, the second configuration, and the third configuration at predetermined time intervals (e.g., multiple times a second). In addition, light sources 330 may be configured to cycle through this combination for various wavelengths of light. During this time, the light detected from light sensors 340 may be collected and examined, as discussed below.

In particular embodiments, light 520, 522 may be emitted by light sources 330 and then detected by light sensors 340 as both backward-scattered light and forward-scattered light. As described above, when controller 310 controls light sources 330 to emit light 520 that penetrates into the body tissue of the user, depending on the wavelength of the light, some of light 520 may be absorbed by the body tissue while some of light 520 will be deflected by certain body tissue or bone. Light 520 deflected may be detected by light sensor 340 as backward-scattered light. In addition, light 522 emitted by light sources 330 on the first portion of optical detection device 210 may penetrate through body tissue of body 220 and deflect in a direction that is within −90° and −180° of the direction of propagation of the emitted light wave or within 90° and 180° of the direction of propagation of the emitted light wave. This light 522 may be detected by light sensor 340 as forward-scattered light.

In particular embodiments, when optical detection device 210 is located on the wrist of the user's body 220, and the user moves one or more fingers as one or more gestures, the moving of the finger may result in the movement of tendons attached to the fingers such that the thickness and location of the tendons slightly change. When light sources 330 are emitting light that is penetrating body tissue, changes occur to the pattern of backward-scattered and forward-scattered NIR light that can be detected by light sensors 340. By having a matrix 530, 540, 550 of light sources 330 and light sensors 340 placed around the wrist, the changes that occur due to the user gesture can be detected.

In addition, as discussed above, controller 310 may be configured to control light sources 330 to operate according to different configurations at predetermined time intervals so that light sensors 340 collect data on backward-scattered light and forward-scattered light for all of these configurations. Moreover, particular characteristics of the signals received by light sensors 340 for particular gestures may be compared with each other based on time series, frequency domains, waveforms, other relevant signal characteristics, or any suitable combination.

Figure 6A:
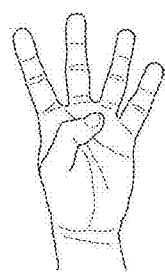
FIGS. 6A-6E illustrate example graphs of signals received by an optical detection device for particular gestures according to particular embodiments of the invention.
Figure 6A:
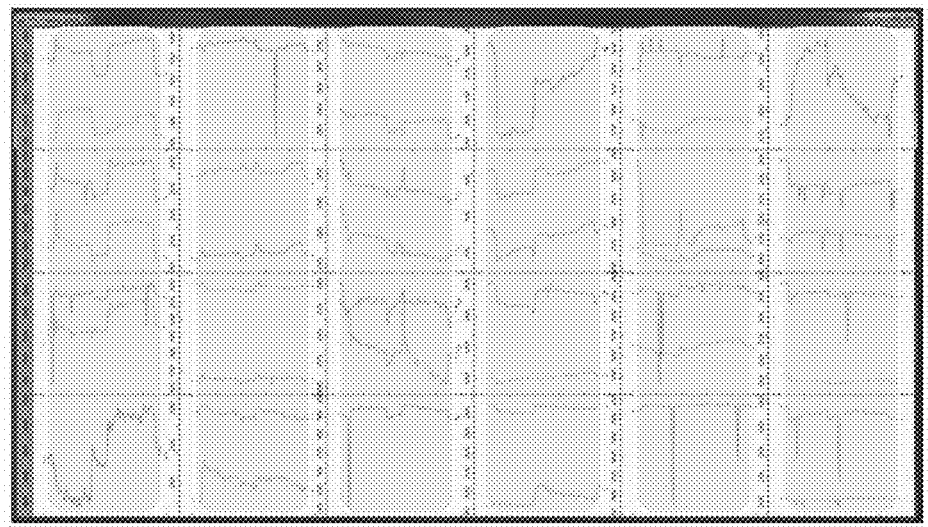
Figure 6B:
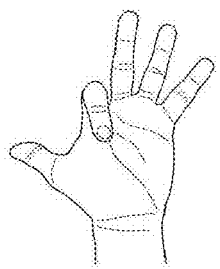
Figure 6B:
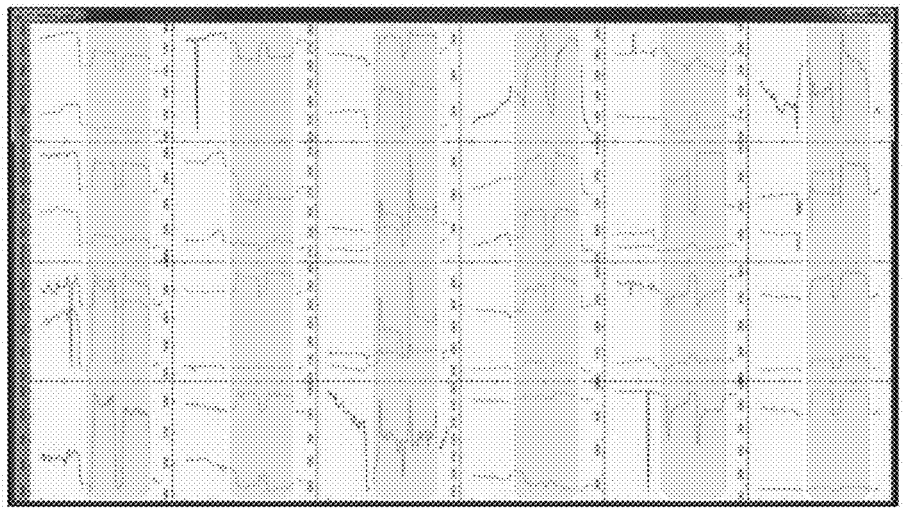
Figure 6C:
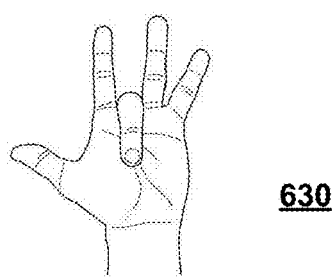
Figure 6C:
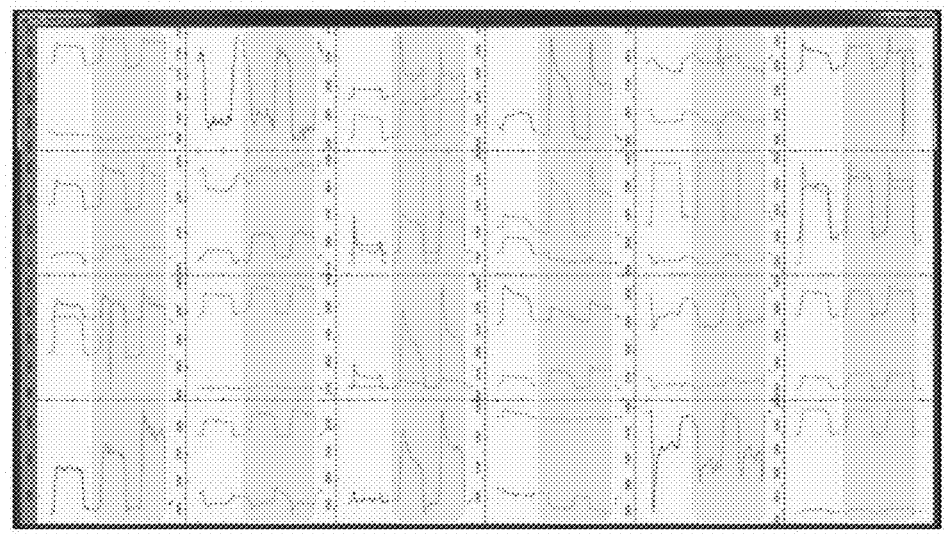
Figure 6D:
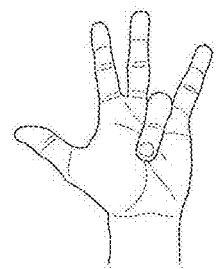
Figure 6D:
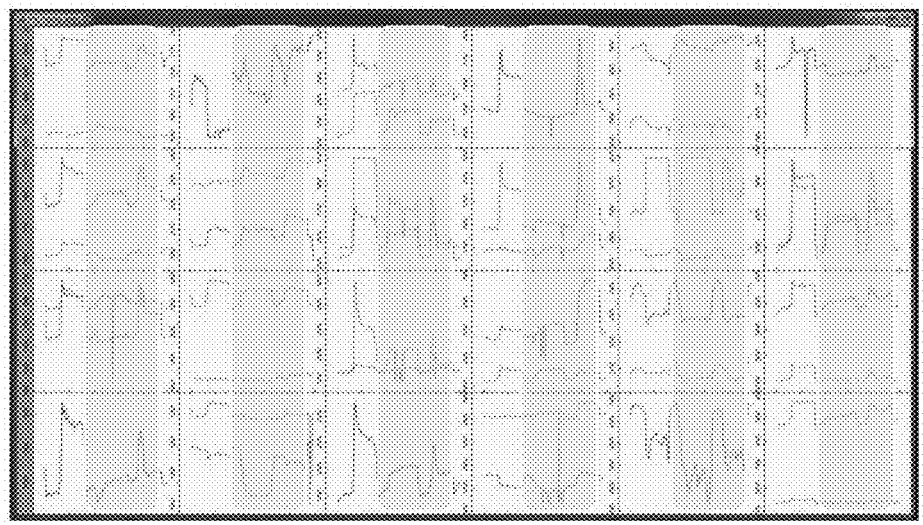
Figure 6E:
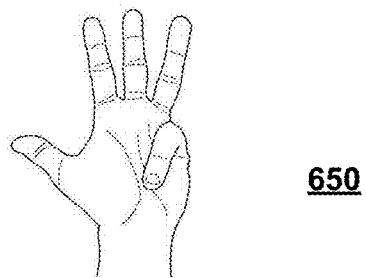
Figure 6E:
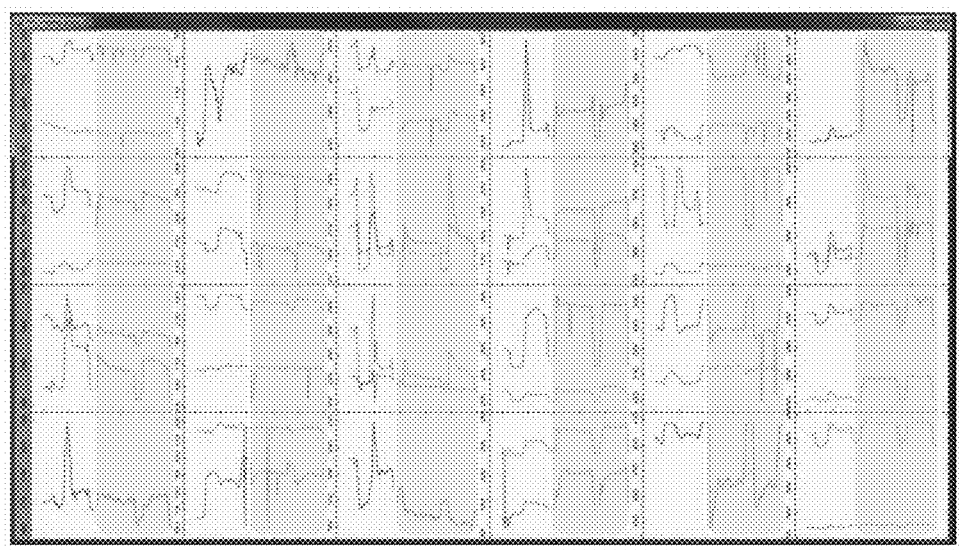

FIGS. 6A-6E illustrate example graphs of signals received for particular gestures according to particular embodiments of the invention. In particular embodiments, graphs 610, 620, 630, 640, and 650 shows the signals received by light sensors 340 based on user gestures. In particular embodiments, when a finger of the user is moved twice, each window of the graph represents the signals received by two photodiodes above and below a LED. As an example and not by way of limitation, FIG. 6A illustrates graph 610 of the signals received when the user moves his thumb, FIG. 6B illustrates graph 620 of the signals received when the user moves his forefinger, FIG. 6C illustrates graph 630 of the signals received when the user moves his middle finger, FIG. 6D illustrates graph 640 of the signals received when the user moves his fourth finger, and FIG. 6E illustrates graph 650 of the signals received when the user moves his pinky finger. As shown in FIGS. 6A-6E, these different gestures resulted in different signals being received by light sensors 340. These signal graphs can be aggregated with data associated with backward-scattered and forward-scattered light outputted at different wavelengths by light sources 330, different configurations of light sources 330 and light sensors 340, and different operations of the light sources 330 at different time intervals to create different spatial patterns of diffusion that can be processed to detect gestures made by the user.

In particular embodiments, other sensors (e.g., accelerometer, gyroscope, other suitable sensor, or any combination thereof) may be used to detect the start of a user gesture and/or interaction (e.g., by detecting the start of a movement). In particular embodiments, these additional sensors may help improve the power consumption of optical detection device 210 by initiating the emitting of light from light sources 330 only when it is determined that certain predetermined conditions (e.g., the detection of movement for more than a predetermined period of time) are satisfied. Although this disclosure describes components and configurations of an optical detection device in a particular manner, this disclosure contemplates components and configurations of the optical detection device in any suitable manner.

APPLICATIONS OF EXAMPLE EMBODIMENTS

In particular embodiments, before optical detection device 210 of optical detection system 200 may be used for gesture recognition for a particular user, optical detection device 210 may first proceed through a calibration process and gesture classification process based on data collected from a large number of users to generate a "standard" scale of readings to be used for gesture recognition, as discussed below. In addition, the data collected from the large number of users may be used to generate a fixed frame of reference used for processing a particular user's gesture information. As discussed above, tendons may be analyzed for detecting gestures associated with a user's hand. As an example, tendons transmit the force of muscle contraction to bones, allowing for the motion of these bones. In addition, fingers are moved by long tendons that deliver motion from the forearm muscles and can be observed to move under the skin at the wrist. In particular, tendons may be observed by using NIR-transmitted light in the wavelengths from 650 nm to 1400 nm. In particular embodiments, as discussed above, optical detection device 210 may comprise a wrist-mounted NIR imaging sensor that may detect finger motion by perceiving changes in the width and position of tendons inside the wrist area based on the backward-scattered and forward-scattered NIR light.

In particular embodiments, optical detection device 210 may first detect a position of the device itself relative to the position of relevant bones in the wrist (e.g., the ulna and radius bones), as discussed below. The location of particular bones can serve as a frame of reference for localizing the device; Accordingly, by detecting bone locations, the optical device 210 can reduce false readings that may occur when the optical detection device 210 moves from a default position on the user's wrist.

These bones may be detected based on the light deflected by the bones, which is different from the light deflected by the rest of body tissue due to the different composition of bone in comparison to other body tissue.

As discussed above, the calibration data may be processed based on the fixed frame of reference (e.g., the one or more bones in the wrist), which can facilitate localizing the device with respect to the user's body (e.g., the specific location on the user's wrist) in order to normalize measurement data and facilitate device calibration. These calibrated measurements of optical detection device 210 may then be used to correct for slippage of the device (e.g., to increase its operational accuracy for gesture recognition), for biometric authentication, for profile identification, and for various other implementations including integration with health monitoring devices and virtual reality systems as an input device, in addition to integration with other existing devices (e.g., devices associated with clothing, jewelry, accessories, etc.).

Preprocessing Phase

Figure 7:
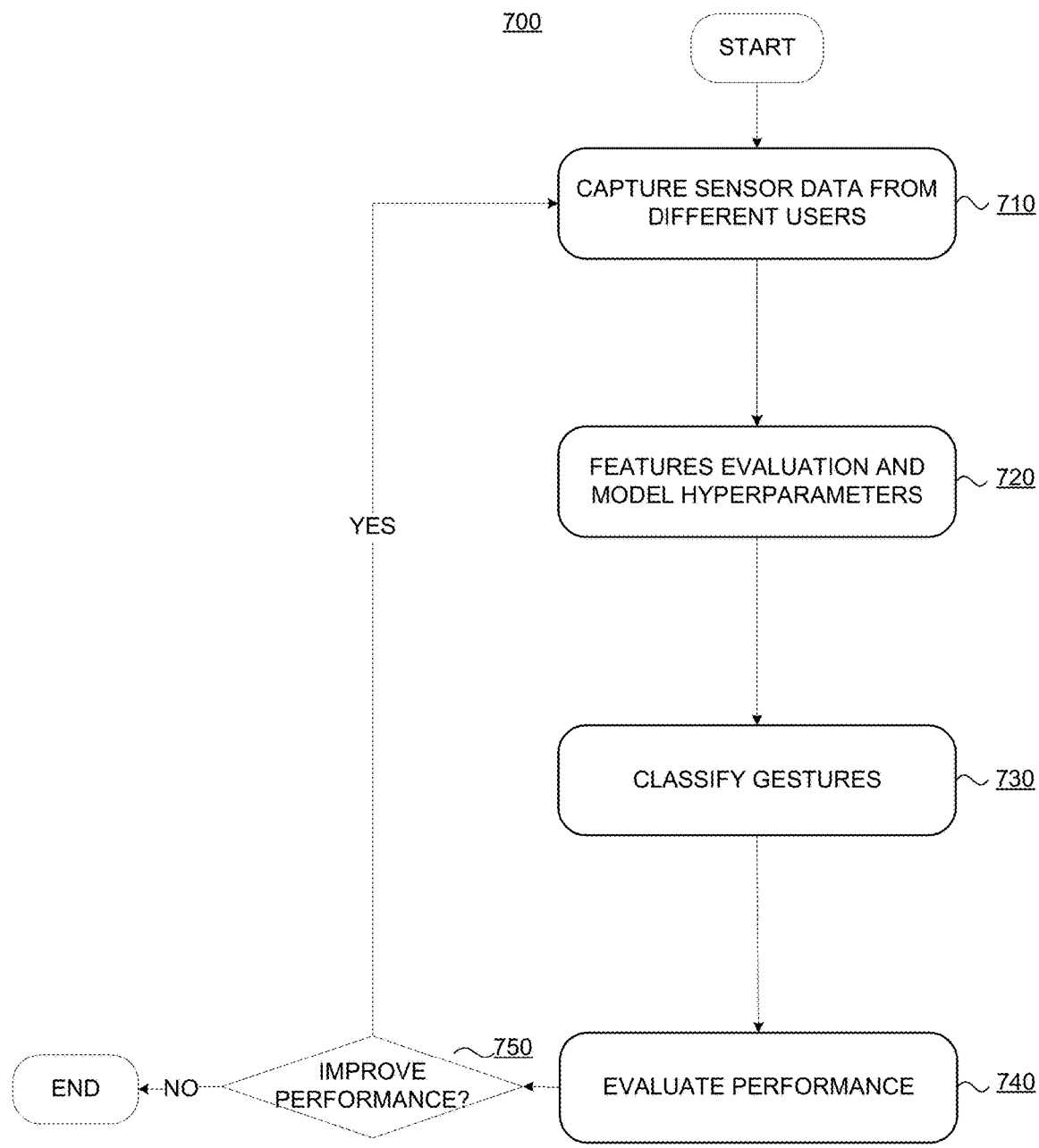
FIG. 7 illustrates an example preprocessing method including a calibration process and a classification process for data collected from a plurality of subjects according to particular embodiments of the invention.

In particular embodiments, a hand-gesture classification preprocessing step may include calibrating optical detection system 200 using a calibration process and a gesture classification process. FIG. 7 illustrates an example preprocessing method 700 including a calibration process and a classification process for data collected from a plurality of subjects according to particular embodiments of the invention. The method begins at step 710, where a number of optical detection devices 210 capture sensor data from different users. In particular embodiments, a hand-gesture classification preprocessing step may include an extensive offline user study step which is executed over a plurality of users following the process described in FIG. 7. The method begins at step 710 where data for a predefined set of gestures is gathered from a plurality of subjects. The data is taken in a controlled environment and further feature evaluation is performed using statistical metrics as features. The statistical metrics are calculated over the raw sensor data for each gesture. They comprise of metrics such as mean, standard deviation, number of peaks, maximum increment and decrement widths, first and second order derivatives of raw data and others. These features form different vectors, which are ranked according to the gesture classification block 730. For each vector of parameters block 730 calculates an accuracy score depending on the number of correctly classified gestures in the user study group. During step 720 the method evaluates the accuracy of 730 taking into account a plurality of values for model hyper parameters that are used in the classification process. These include parameters such us dimensionality of the feature vector (length of the parameter vectors), regularization parameters and others. Step 740 selects the calibration parameters that produce best results in the user research.

In particular embodiments, optical detection device 210 may detect and collect sensor data (e.g., raw sensor data as shown in FIGS. 6A-6E) from light sensors 340 from a plurality of users participating in a machine learning training process. The collected sensor data may be collected for one or more particular gestures based on a controlled environment of a specific calibration sequence. As an example and not by way of limitation, the calibration process used as part of the machine learning process may include a specific calibration sequence including different gestures: (1) a starting position of a first gesture in which all the fingers are held together in a first, (2) a thumb gesture in which all fingers except the thumb are held together in a first, and the thumb is held straight and pointed forward, (3) a two-finger gesture including all fingers except the thumb and the index finger being held in a first, and the thumb and index finger are held straight and pointing forward, and (4) an ending position of an open-hand gesture in which all fingers are held straight and pointing forward. This calibration sequence may allow for the detection of large tendon movements and differences between the movements, and data associated with each of the different gestures may be collected from each user for the machine learning training process. In particular embodiments, this gesture sensor data may be collected and used as the pre-classification calibration data. In particular embodiments, the sensor data and pre-classification calibration data may be stored on any suitable database such as data store 140. The calibration parameters may include a matrix transformation to be applied to the raw sensor data during the operation of optical device 210. The calibration parameters may include may include the hyper parameters producing the best accuracy for the machine learning models used in optical detection system 200. The calibration parameters are chosen such that they maximize efficiency between different subjects taking part in an extensive offline user study.

At step 720, preprocessing method 700 may include a features evaluation process for all sensor data from step 710. The features evaluation process may be used to determine a plurality of "features," which includes distinctive attributes associated with these users that can determined from the collected calibration data. For example, a particular feature vector (e.g., an ordered list of features) of a user can be linked to a gesture.

The features evaluation process may include the normalization of feature data from the calibration data from the raw data collected in the steps discussed above. The features evaluation process may also include determining a plurality of features. As an example and not by way of limitation, for each light sensor 340, a features vector may include a set of corresponding absorption-statistics features that are determined based on how much light has been absorbed by light sensors 340. As another example and not by way of limitation, based on data that light deflected by the wrist and arm bones is distinguishable from light deflected by the rest of the wrist tissue, the features vector may include bone-detection features that are determined based on data from light sensors 340 The bone-detection features may be used to determine positioning of optical detection device 210 on the wrist, as discussed below. As yet another example and not by way of limitation, the features vector may include additional biometrics data such as metrics related to human characteristics that are determined based on the placement of the device and parameters such as electrocardiogram (ECG) rates, electromyography (EMG) rates, heart and respiratory rates, blood pressure, other suitable parameters, or any combination thereof. In particular embodiments, the features data and features vectors may be stored on any suitable database such as data store 140.

At step 730, preprocessing method 700 may include a gesture classification process for optical detection device 210. In particular embodiments, the calibration data may be evaluated using one or more machine learning models such as k-nearest neighbors (k-NN), support vector machine (SVM) models, other suitable models, or any combination thereof. In addition, the classification of the gestures may be determined based on classification techniques such as an one-verses-all (OvA) multiclass classification technique, one-verses-one (OvO) reduction technique, other suitable techniques, or any combination thereof. At step 740, preprocessing method 700 may include a performance evaluation process for optical detection device 210. In evaluating the performance of the process, the method may determine a classification rate based on n number of correct samples over n number of all samples. In particular embodiments, this classification data may be stored on any suitable database such as data store 140.

Then, at step 750, preprocessing method 700 may include determining whether performance of optical detection device 210 has improved based on the captured sensor data. In particular embodiments, preprocessing method 700 determine whether each round of captured sensor data provides more information for the machine learning process to improve the gestures classification, or whether the additional data is no longer adding any statistically-significant information to the machine learning process. If the determination is YES, preprocessing method 700 may return back to step 710 to capture additional sensor data from different subjects. If the determination is NO, preprocessing method 700 may terminate.

Although this disclosure describes a preprocessing method for optical detection system 200 in a particular manner, this disclosure contemplates a preprocessing method for optical detection system 200 in any suitable manner.

Gesture Recognition

In particular embodiments, a gesture recognition process for optical detection system 200 may include detecting bone structures to determine a frame of reference based on the fixed positions of the bone structures. As discussed above, the calibration data may be processed based on the fixed frame of reference (e.g., the one or more bones in the wrist), which can facilitate localizing the device with respect to the user's body (e.g., the specific location on the user's wrist), reduce false readings due to slippage of optical detection device 210, and improve the gesture recognition process.

Figure 8:
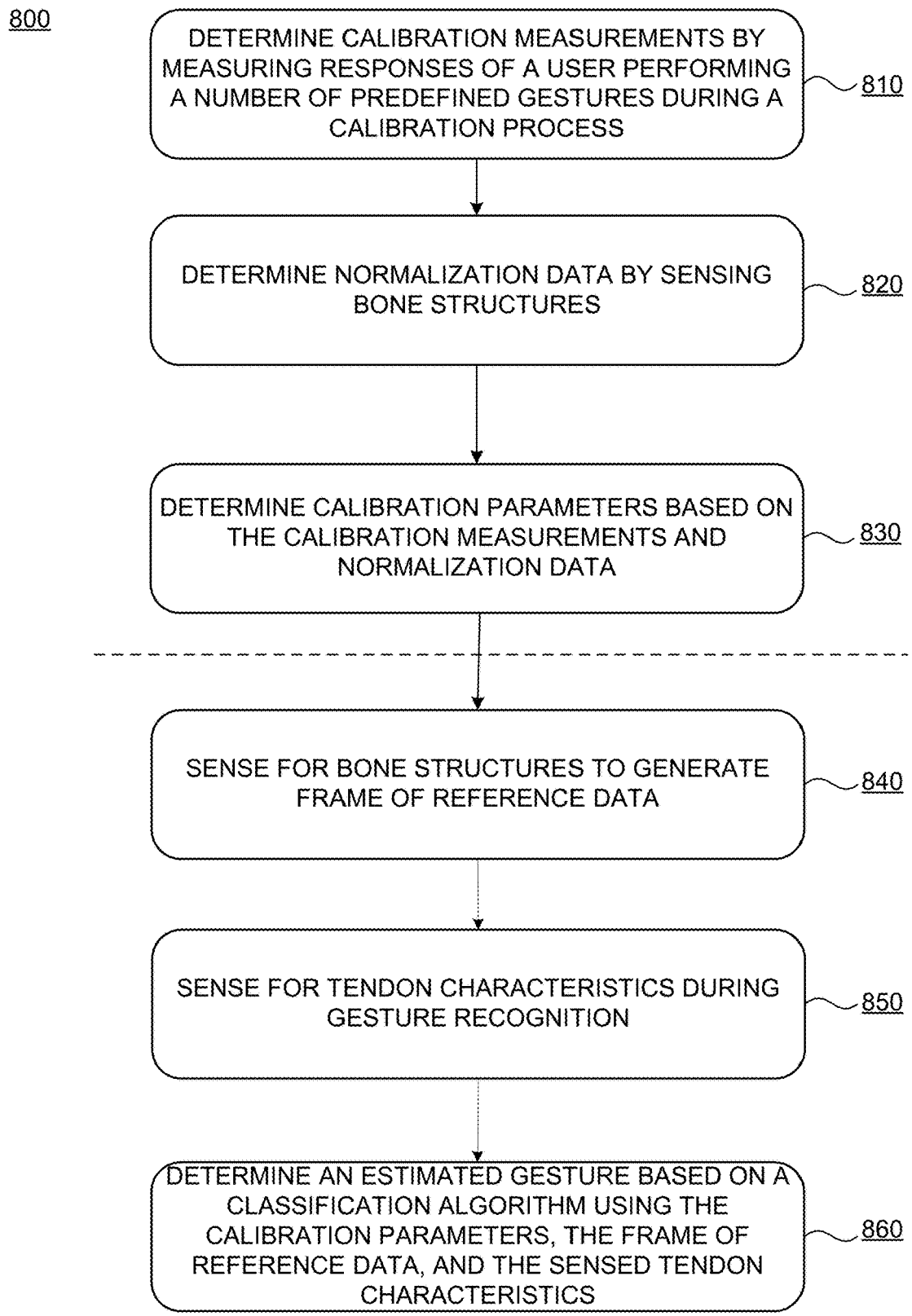
FIG. 8 illustrates an example method for gesture recognition according to particular embodiments of the invention.

FIG. 8 illustrates an example method 800 for gesture recognition according to particular embodiments of the invention. Steps 810, 820, and 830 are associated with a calibration phase in which calibration measurements may be collected and analyzed for a specific user. The method begins at step 810, optical detection system 200 may determine calibration measurements by measuring responses of a user performing a number of predefined gestures during a calibration process. This calibration process and the collected calibration measurements may be used to augment the calibration parameters derived from an offline user study as described in preprocessing method 700, discussed above.

At step 820, optical detection system 200 may determine bone calibration parameters by sensing bone structures. As discussed above, bones such as the ulna and radius bones may be detected and distinguished from other body tissue based on light detected by light sensors 340. These bone structure measurements may be determined for each of the plurality of users by a single device on each single user.

At step 830, optical detection system 200 may take as an input the calibration measurements comprising of raw sensor data from step 810 for a single subject. Step 830 uses the calibration parameters, which are an output from the preprocessing method 700, as well as the bone calibration parameters from step 820 for the same user. These sets of parameters are represented as vectors and may be applied consequently as matrix transformations on the raw sensor data detected by the optical detection system 200. The final output after all matrix multiplications is the feature vector used during the training and classification steps of the machine learning algorithm described below. In particular embodiments, the calibration measurements, bone structure measurements, and calibration parameters may be stored on any suitable database such as data store 140.

Steps 840, 850, and 860 are associated with a gesture recognition phase in which a particular user's gesture may be determined. At step 840, optical detection system 200, via optical detection device 210, may sense for bone structures to generate frame of reference data. At step 850, optical detection system 200, via optical detection device 210, may sense for tendon characteristics during gesture recognition. As discussed above, bones and body tissue may be detected and distinguished from each other based on light detected by light sensors 340. Then, at step 860, optical detection system 200 may determine an estimated gesture based on a classification algorithm using the calibration parameters (e.g., determined based on a plurality of users), the frame of reference data (e.g., associated with the particular user), and the sensed tendon characteristics (e.g., associated with the particular user). In particular embodiments, the frame of reference data and tendon characteristics data may be stored on any suitable data storage device such as data store 140, or alternatively may be stored on any device associated with optical detection system 200 (e.g., optical detection device 210, mobile electronic device 230, etc.) due to the personal nature of the user data. Calibration steps 810-830 may occur one time for a user and/or based on user request. Step 840 may be repeated at a different frequency than steps 850 and 860. Step 840 may be repeated periodically and less frequently than steps 850 and 860, or may be executed based on detection of movement, activity, poor performance of optical detection system 200, other suitable detection of a condition that may indicate slippage of optical detection system 200, or any combination thereof.

Figure 9:
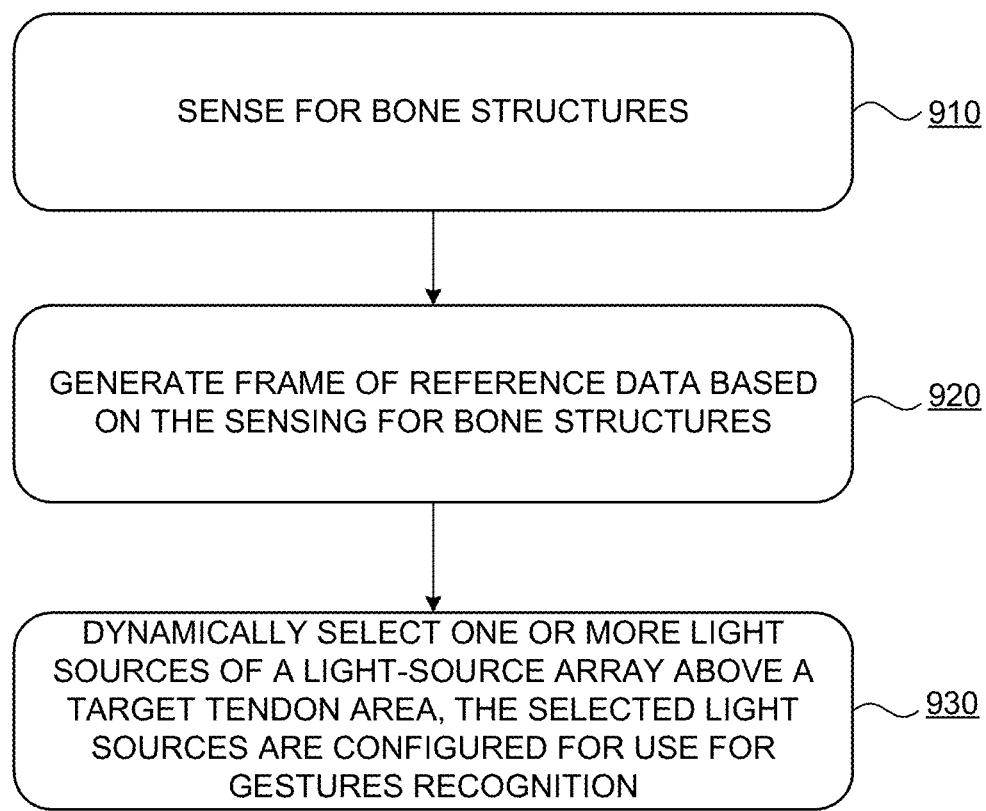
FIG. 9 illustrates an example method for operating the optical detection device based on detected bone according to some embodiments of the invention.

In particular embodiments, the detected bone structures may be used for the operation of light sources 330 and light sensors 340 of optical detection device 210. FIG. 9 illustrates an example method 900 for operating optical detection device 210 based on detected bone according to particular embodiments of the invention. The method begins at step 910, where optical detection system 200, via optical detection device 210, may sense for bone and tissue structures. At step 920, optical detection system 200 may generate frame of reference data based on the sensing for bone structures. This sensing for bone structures and generating frame of reference data may be similarly to steps 840 and 850 of gesture-recognition method discussed above.

At step 930, optical detection system 200 may dynamically select one or more light sources of a light-source array above a target tendon area, wherein the selected light sources are configured for use for gestures recognition. In addition, optical detection system 200 may determine bone structures such as location of a particular bone relative to the location of the tendon structures that exhibited the change in characteristics. Moreover, the frame of reference data may be used to determine the location and/or orientation of optical detection device 210 relative to the user's wrist. Thus, optical detection 200 may then dynamically select one or more light sources 330 that are located above the target tendon area to emit light to be captured by light sensor 340 in order to maximize efficiency of the light-source array while minimizing power consumption. In particular embodiments, the bone structure measurements, frame of reference data, target tendon area data, and data on the dynamically selected light sources may be stored on any suitable data such as data store 140, or alternatively may be stored on any device associated with optical detection system 200 (e.g., optical detection device 210, mobile electronic device 230, etc.) due to the personal nature of the user data. Although this disclosure describes gesture recognition process for optical detection system 200 in a particular manner, this disclosure contemplates gesture recognition process for optical detection system 200 in any suitable manner.

Slippage Corrector

Figure 10:
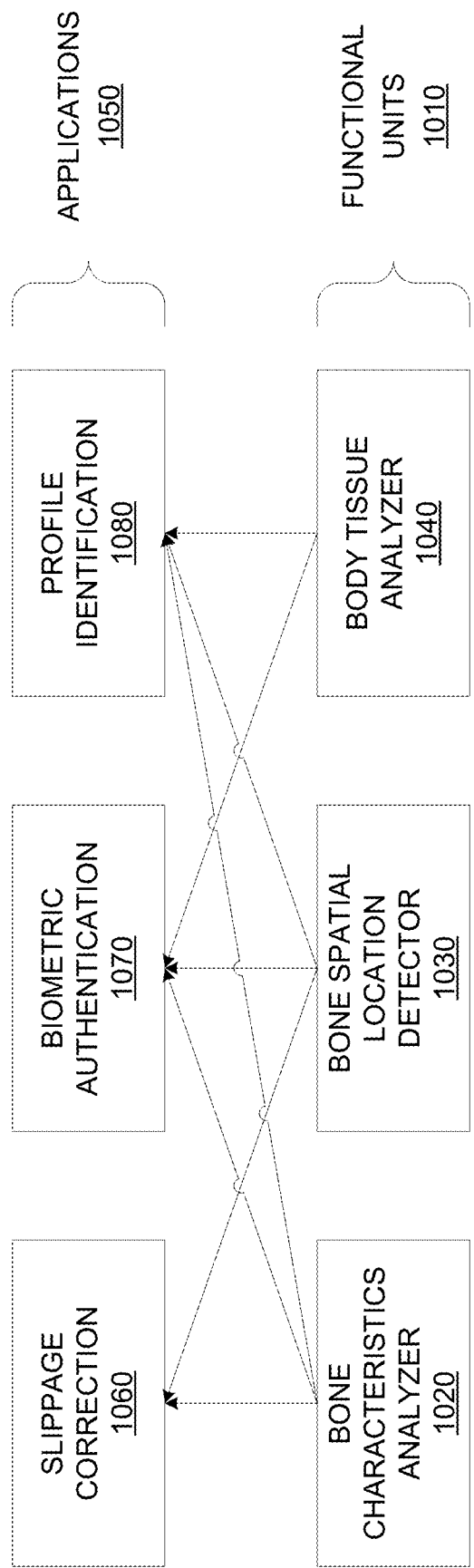
FIG. 10 illustrates example applications of the optical detection system according to particular embodiments of the invention.

FIG. 10 illustrates example functional units and applications of optical detection system 200 according to particular embodiments of the invention. These example functional units and applications of optical detection system 200 may be implemented by program code stored in memory coupled to one or more processors. In particular embodiments, optical detection system 200 may comprise functional units 1010 including a bone characteristics analyzer 1020, a bone spatial location detector 1030, and a body tissue analyzer 1040, and applications 1050 including a slippage correction application 1060, a biometric authentication application 1070, and a profile identification application 1080. Bone characteristics analyzer 1020 may be configured to determine characteristics of bones of one or more users, which may include intrinsic bone characteristics such as the size of bones, density of bones, whether the bones have been previously broken, the location of bones relative to other body tissue, other relevant bone characteristics, or any combination thereof. Bone spatial location detector 1030 may be configured to determine the location of bones of one or more users, which may include the location of one or more bones as a frame of reference measurement, the location of one or more bones relative to other bones, other relevant bone-location characteristics, or any combination thereof. Body tissue analyzer 1040 may be configured to determine characteristics of body tissue of one or more users, including the size/thickness of body tissue, the density of body tissue, the location of body tissue, other relevant body-tissue characteristics, or any combination thereof.

In particular embodiments, as shown by the arrows in FIG. 10, bone characteristics analyzer 1020, bone spatial location detector 1030, and body tissue analyzer 1040 may be used for slippage correction application 1060. As discussed above, false readings may result from slippage of optical detection device 210 from a predefined "default" position, and thus localizing the position of the device with respect to the user's body by determining how much the device has moved (e.g., "slipped") from the default position may help in the gesture recognition process.

Figure 11:
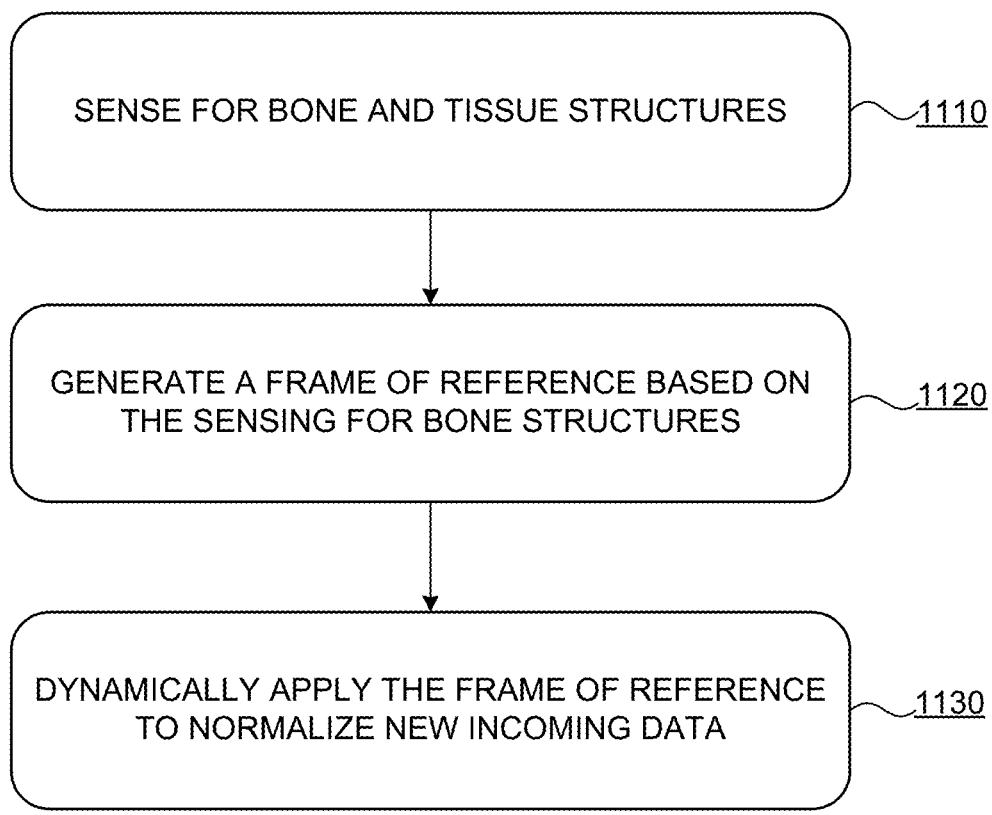
FIG. 11 illustrates an example method for device slippage correction according to particular embodiments of the invention.

FIG. 11 illustrates an example method 1100 for device slippage correction according to particular embodiments of the invention. The method begins at step 1110, where optical detection system 200, via bone characteristics analyzer 1020 of optical detection device 210, may sense for bone structures of a user. In particular embodiments, controller 310 controls light sources 330 to emit light in a plurality of different patterns (e.g., discussed above with respect to FIGS. 5E-5G) and using a plurality of different wavelengths in the optical window (e.g., discussed above with respect to FIG. 3B), and collects light scatter information (e.g., including backward-scattered and forward-scattered light, as discussed above) from light sensors 340.

At step 1120, optical detection system 200 may generate a frame of reference based on the sensing for bone structures. In particular embodiments, bone spatial location detector 1030 may detect the location of one or more bones as frame of reference data for the location and orientation of optical detection system 210. In addition, optical detection system 200 may preprocess the collected raw data to remove noise, project the raw data into a lower dimensional space and extract key statistical information corresponding to how much light has been absorbed by each light sensor 340 in each configuration discussed above (e.g., combination of light patterns and wavelengths of light used). The statistical data may include calculating values such as mean, standard deviation, and root mean square. Methods such as Principal Component Analysis (PCA) may be used for dimensionality reduction of the raw feature vector which helps the machine learning model described below achieve better accuracy scores among a plurality of users. Then, optical detection system 200 may extract a normalization vector as a frame of reference in the specified subspace.

At step 1130, optical detection system 200 may dynamically apply the frame of reference to normalize new incoming data. In particular embodiments, the frame of reference data may be used to improve the classification algorithms in the gesture recognition process by applying each new set of collected data to the preprocessing calibration method (e.g., discussed with respect to FIG. 7). In addition, this normalization data (i.e., frame of reference data) may be applied as a vector-space transformation to each new data sample taken by a specific device (e.g., optical detection system 210). In other words, classification algorithms are determined based on data from on a large number of users who perform particular gestures in a controlled environment are collected into a database, and when a new user first uses an optical detection device, the new user may be asked to perform certain calibration gestures similar to the gestures performed by the users in the controlled environment so that the system may determine where in the database of gesture information and/or based on classification algorithms that the new user mostly closely matches with. In particular embodiments, the calibration data and classification algorithms may be stored on network 130, server 140, or data store 150, and the new-user-specific data may be stored on one or more devices of optical detection system 200 or on network 130, server 140, or data store 150. Although this disclosure describes a slippage corrector of optical detection system 200 in a particular manner, this disclosure contemplates a slippage corrector of optical detection system 200 in any suitable manner.

Biometric Authenticator

Figure 12:
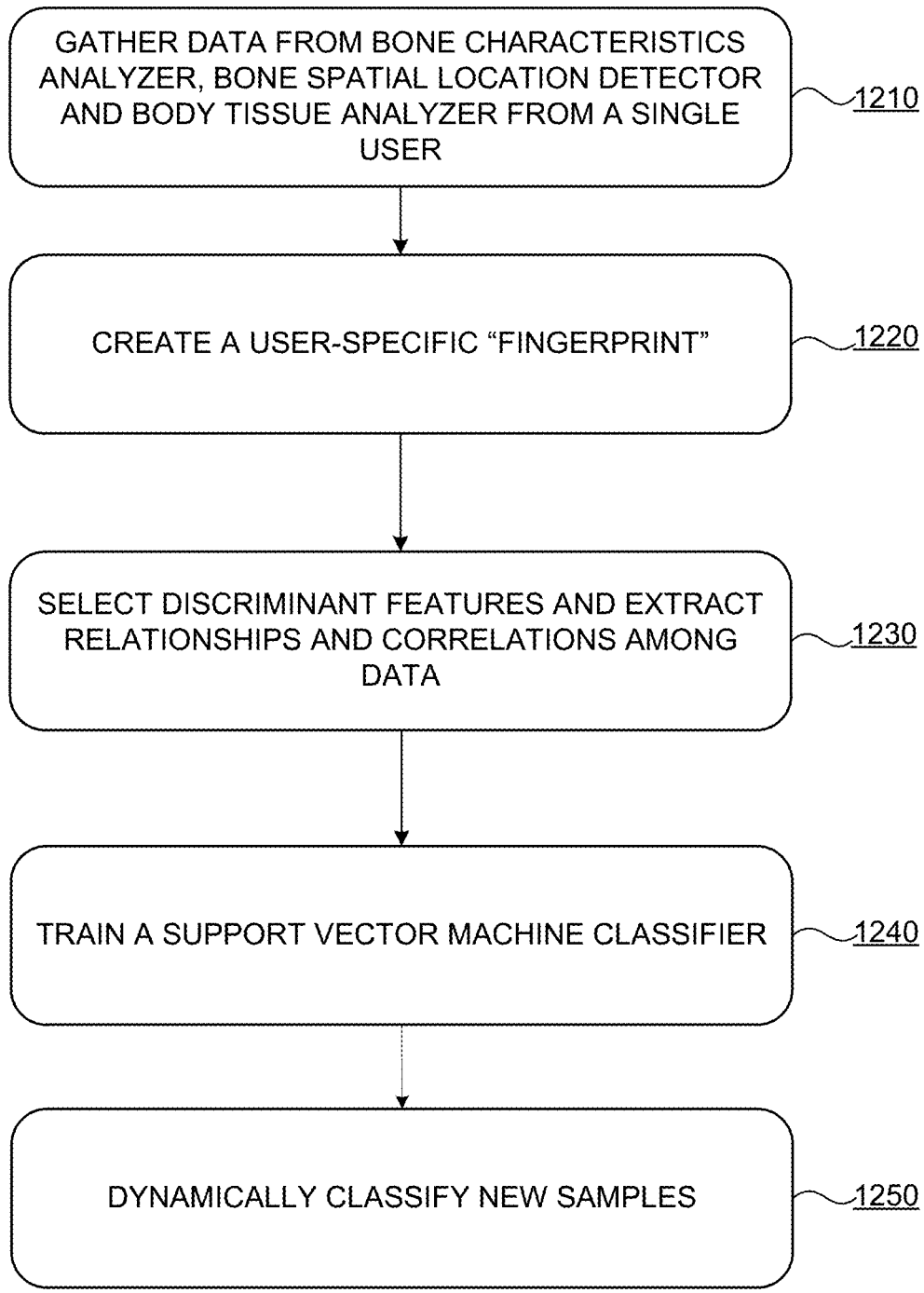
FIG. 12 illustrates an example method for biometric authentication according to particular embodiments of the invention.

In particular embodiments, as shown by the arrows in FIG. 10, bone characteristics analyzer 1020, bone spatial location detector 1030, and body tissue analyzer 1040 may be used for biometric authentication application 1070. Biometric authentication application 1070 may include technologies for measuring and analyzing biological characteristics of users to verify user identify for authentication and secure access. As an example, user bone characteristics are unique for each user, and thus they may be used for identification and authentication purposes such as device unlocking (e.g., phone unlocking), signing into accounts (e.g., for personal accounts, parent controls, administrator access, etc.), block age-restricted content (e.g., by determining the identify or age of a user), other relevant purposes, or any combination thereof. FIG. 12 illustrates an example method 1200 for biometric authentication according to particular embodiments of the invention. The method begins at step 1210, where optical detection system 200 may gather data from bone characteristics analyzer 1020, bone spatial location detector 1030, and body tissue analyzer 1040 from a single user. The data may include all data specific to each user, including observable parameters of bones and other body tissue under NIR light such as spatial location, size, material density, mineral structure, other suitable parameters, or any combination thereof. At step 1220, optical detection system 200 may create a user-specific "fingerprint." This "fingerprint" may become a feature vector (discussed above). In addition, this user-specific "fingerprint" vector which may then be further processed and used in the training of the classification algorithm by applying each new set of collected data to the preprocessing calibration method (e.g., discussed with respect to FIG. 7).

At step 1230, optical detection system 200 may select discriminant features (e.g., features that distinguish the specific user with other users in the database) and extract relationships and correlations among data (e.g., for use in authentication purposes). In particular embodiments, this step may be done automatically by optical detection system 200. Then, at step 1240, optical detection system 200 will user the collected data for a plurality of users to train a Support Vector Machine model to be used in biometric authentication application 1070. This process includes both a training procedure and test procedure. Step 1240 will create an SVM model to maximize the distance between support vectors in the higher dimensional feature space of the data belonging to the different users already in the database. The classifier would then position each new test sample in this higher dimensional space, determine its location based on the support vectors and use this information to predict the correct class. Lastly, at step 1250, optical detection system 200 may dynamically classify new samples. In particular embodiments, new samples from new users may be taken and classified for the purpose of authentication when the biometric authenticator is used. In addition, classification algorithms are determined based on data from on a large number of users (e.g., including user-specific characteristics of bone and other body tissue) that is collected into a database, and when a new user is added for the purpose of authentication, the new user's characteristics of bone and other body tissue is determined to classify the user data based on classification algorithms in order to differentiate the user's biometric characteristics with other users in the database. In particular embodiments, the classification algorithms and user biometric characteristics may be stored on network 130, server 140, or data store 150, and the new-user-specific data (e.g., the user-specific "fingerprint" data) may be stored on one or more devices of optical detection system 200 or on network 130, server 140, or data store 150. Although this disclosure describes biometric authenticator of optical detection system 200 in a particular manner, this disclosure contemplates a biometric authenticator of optical detection system 200 in any suitable manner.

Profile Identifier

Figure 13:
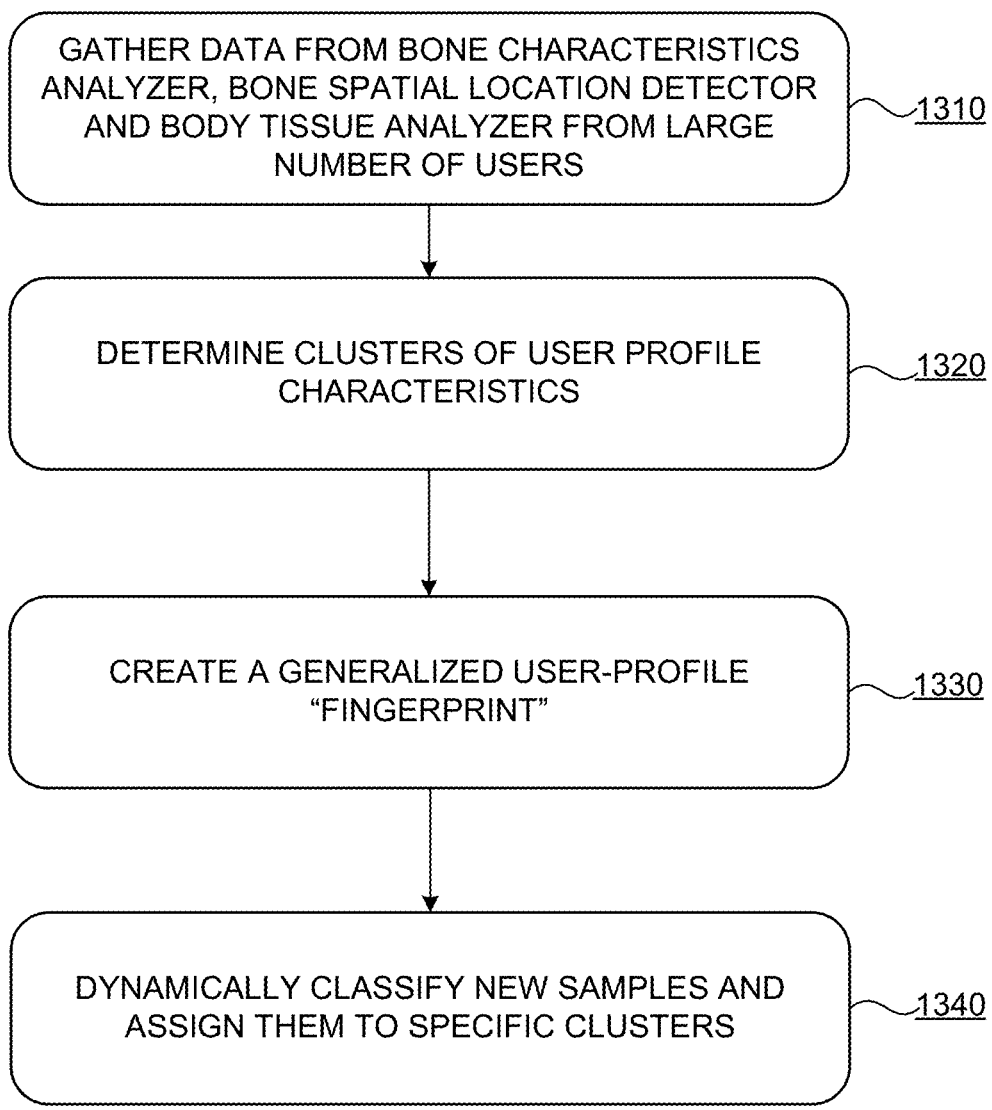
FIG. 13 illustrates an example method for profile identification according to particular embodiments of the invention.

In particular embodiments, as shown by the arrows in FIG. 10, bone characteristics analyzer 1020, bone spatial location detector 1030, and body tissue analyzer 1040 may be used for profile identification application 1080. Profile identification application 1080 may include technologies for identifying the profile of a user wearing optical detection device 210. User profile may include information on their age, sex, gender, height, weight race, ethnicity, lifestyle, other relevant information, or any combination thereof. As an example and not by way of limitation, this information may be used for advertisement purposes, content selection purposes (e.g., content to be display to a user), device configuration purposes (e.g., providing bigger text size for older user, colorful UIs for children, etc.), other suitable purposes, or any combination thereof. FIG. 13 illustrates an example method 1300 for profile identification according to particular embodiments of the invention. The method begins at step 1310, where optical detection system 200 may gather data from bone characteristics analyzer 1020, bone spatial location detector 1030, and body tissue analyzer 1040 from a large number of users. In particular embodiments, this data may be mapped against the profile of a particular user, which may include user-specific information of the particular user such as age, sex, gender, height, weight race, ethnicity, lifestyle, other relevant information, or any combination thereof.

At step 1320, optical detection system 200 may determine clusters of user profile characteristics. In particular embodiments, optical detection system 200 may apply clustering techniques (e.g., k-means clustering, Gaussian mixture model, etc.) over the raw data in order to analyze and determine the possible clusters based on the premise of maximizing the distance between the possible clusters' centers in the higher dimensional space of the feature vector generated by the user profile characteristics. At step 1330, optical detection system 200 may create a generalized user-profile "fingerprint." In particular embodiments, each user-profile "fingerprint" may correspond to a cluster of different user profile characteristics. Then, at step 1340, optical detection system 200 may dynamically classify new samples and assign them to specific clusters. In particular embodiments, the new samples are dynamically classified using classification algorithms (e.g., linear discriminant analysis (LDA), k-NN, etc.) in order to classify each new sample into a specific group each time the profile identifier is used to generate a profile for a new user. In particular embodiments, the classification algorithms and clusters of user profile characteristics may be stored on network 130, server 140, or data store 150, and the new-user-specific data (e.g., the user-profile "fingerprint" data) may be stored on one or more devices of optical detection system 200 or on network 130, server 140, or data store 150. Although this disclosure describes a profile identifier of optical detection system 200 in a particular manner, this disclosure contemplates a profile identifier of optical detection system 200 in any suitable manner.

Other Uses

In particular embodiments, the systems and embodiments described above may be integrated with wearable health technology devices to perform health-related monitoring tasks (e.g., monitoring heartrate, stress levels, etc.), gesture recognition, tracking of movements (e.g., during rehabilitation), other relevant tasks, or any combination thereof.

In particular embodiments, the systems and embodiments described above may be used to improve the accuracy for an input device for virtual-reality (VR) environments. As an example and not by way of limitation, the systems and embodiments may be implemented as a head tracking device by determination the orientation of a user's point of view and sending that information to a VR system. The head tracking device may be used for eye-referenced images which may operate such that the user's eyes moving in that particular direction results in the user's view shifts up, down, left, or right. In addition, the head tracking device may be used for navigation based on head movements, which may operate such that a user's tilting of his head at an angle or moving his head forward or backward (e.g., without changing the angle of his gaze) results in the user's view shifting in that angle, or forward or backward. As another example and not by way of limitation, the systems and embodiments may be implemented as a hand tracking device that can track the movement of a user's hands in VR environments. This may allow for the translation of movements of the user's real hand to the virtual hand in the VR environment, in addition to the direct manipulation of virtual objects in an intuitive way, communication with other users (e.g., using body language, sign language, etc.). As yet another example and not by way of limitation, the systems and embodiments may be implemented as a body tracking device that can sense the movement of body (e.g., the movement of the legs, feet, arms, hands, head, torso, etc.) and translate the movements of the user's real body to the virtual body in the VR environment. This may allow for user interactions with other users using the user's avatar, walking around in the VR environment, detection for navigation within the VR environment, etc.

In particular embodiments, the systems and embodiments described above may also be integrated with clothes, jewelry, and other accessories, to perform gesture recognition, movement tracking, other relevant tasks, or any combination thereof.

Figure 14:
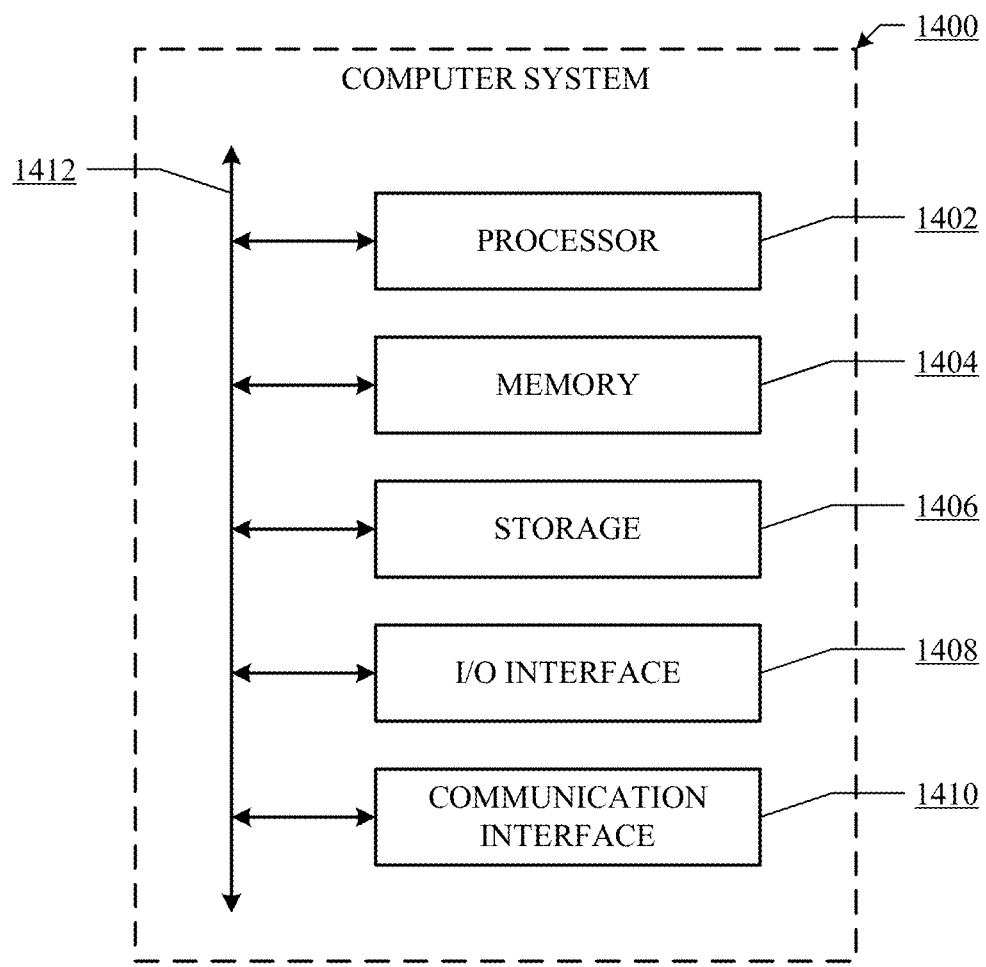
FIG. 14 illustrates an example computer system according to particular embodiments of the invention.

Although this disclosure describes particular uses of optical detection system 200 in a particular manner, this disclosure contemplates any other uses of optical detection system 200 in any suitable manner Systems and Methods FIG. 14 illustrates an example computer system 1400 according to some embodiments of the invention. In particular embodiments, one or more computer systems 1400 perform one or more steps of one or more methods described or illustrated herein. In particular embodiments, one or more computer systems 1400 provide functionality described or illustrated herein. In particular embodiments, software running on one or more computer systems 1400 performs one or more steps of one or more methods described or illustrated herein or provides functionality described or illustrated herein. Particular embodiments include one or more portions of one or more computer systems 1400. Herein, reference to a computer system may encompass a computing device, and vice versa, where appropriate. Moreover, reference to a computer system may encompass one or more computer systems, where appropriate.

This disclosure contemplates any suitable number of computer systems 1400. This disclosure contemplates computer system 1400 taking any suitable physical form. As example and not by way of limitation, computer system 1400 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, or a combination of two or more of these. Where appropriate, computer system 1400 may include one or more computer systems 1400; be unitary or distributed; span multiple locations; span multiple machines; span multiple data centers; or reside in a cloud, which may include one or more cloud components in one or more networks. Where appropriate, one or more computer systems 1400 may perform without substantial spatial or temporal limitation one or more steps of one or more methods described or illustrated herein. As an example and not by way of limitation, one or more computer systems 1400 may perform in real time or in batch mode one or more steps of one or more methods described or illustrated herein. One or more computer systems 1400 may perform at different times or at different locations one or more steps of one or more methods described or illustrated herein, where appropriate.

In particular embodiments, computer system 1400 includes a processor 1402, memory 1404, storage 1406, an input/output (I/O) interface 1408, a communication interface 1410, and a bus 1412. Although this disclosure describes and illustrates a particular computer system having a particular number of particular components in a particular arrangement, this disclosure contemplates any suitable computer system having any suitable number of any suitable components in any suitable arrangement.

In particular embodiments, processor 1402 includes hardware for executing instructions, such as those making up a computer program. As an example and not by way of limitation, to execute instructions, processor 1402 may retrieve (or fetch) the instructions from an internal register, an internal cache, memory 1404, or storage 1406; decode and execute them; and then write one or more results to an internal register, an internal cache, memory 1404, or storage 1406. In particular embodiments, processor 1402 may include one or more internal caches for data, instructions, or addresses. This disclosure contemplates processor 1402 including any suitable number of any suitable internal caches, where appropriate. As an example and not by way of limitation, processor 1402 may include one or more instruction caches, one or more data caches, and one or more translation lookaside buffers (TLBs). Instructions in the instruction caches may be copies of instructions in memory 1404 or storage 1406, and the instruction caches may speed up retrieval of those instructions by processor 1402. Data in the data caches may be copies of data in memory 1404 or storage 1406 for instructions executing at processor 1402 to operate on; the results of previous instructions executed at processor 1402 for access by subsequent instructions executing at processor 1402 or for writing to memory 1404 or storage 1406; or other suitable data. The data caches may speed up read or write operations by processor 1402. The TLBs may speed up virtual-address translation for processor 1402. In particular embodiments, processor 1402 may include one or more internal registers for data, instructions, or addresses. This disclosure contemplates processor 1402 including any suitable number of any suitable internal registers, where appropriate. Where appropriate, processor 1402 may include one or more arithmetic logic units (ALUs); be a multi-core processor; or include one or more processors 1402. Although this disclosure describes and illustrates a particular processor, this disclosure contemplates any suitable processor.

In particular embodiments, memory 1404 includes main memory for storing instructions for processor 1402 to execute or data for processor 1402 to operate on. As an example and not by way of limitation, computer system 1400 may load instructions from storage 1406 or another source (such as, for example, another computer system 1400) to memory 1404. Processor 1402 may then load the instructions from memory 1404 to an internal register or internal cache. To execute the instructions, processor 1402 may retrieve the instructions from the internal register or internal cache and decode them. During or after execution of the instructions, processor 1402 may write one or more results (which may be intermediate or final results) to the internal register or internal cache. Processor 1402 may then write one or more of those results to memory 1404. In particular embodiments, processor 1402 executes only instructions in one or more internal registers or internal caches or in memory 1404 (as opposed to storage 1406 or elsewhere) and operates only on data in one or more internal registers or internal caches or in memory 1404 (as opposed to storage 1406 or elsewhere). One or more memory buses (which may each include an address bus and a data bus) may couple processor 1402 to memory 1404. Bus 1412 may include one or more memory buses, as described below. In particular embodiments, one or more memory management units (MMUs) reside between processor 1402 and memory 1404 and facilitate accesses to memory 1404 requested by processor 1402. In particular embodiments, memory 1404 includes random access memory (RAM). This RAM may be volatile memory, where appropriate Where appropriate, this RAM may be dynamic RAM (DRAM) or static RAM (SRAM). Moreover, where appropriate, this RAM may be single-ported or multi-ported RAM. This disclosure contemplates any suitable RAM. Memory 1404 may include one or more memories 1404, where appropriate. Although this disclosure describes and illustrates particular memory, this disclosure contemplates any suitable memory.

In particular embodiments, storage 1406 includes mass storage for data or instructions. As an example and not by way of limitation, storage 1406 may include a hard disk drive (HDD), a floppy disk drive, flash memory, an optical disc, a magneto-optical disc, magnetic tape, or a Universal Serial Bus (USB) drive or a combination of two or more of these. Storage 1406 may include removable or non-removable (or fixed) media, where appropriate. Storage 1406 may be internal or external to computer system 1400, where appropriate. In particular embodiments, storage 1406 is non-volatile, solid-state memory. In particular embodiments, storage 1406 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 1406 taking any suitable physical form. Storage 1406 may include one or more storage control units facilitating communication between processor 1402 and storage 1406, where appropriate. Where appropriate, storage 1406 may include one or more storages 1406. Although this disclosure describes and illustrates particular storage, this disclosure contemplates any suitable storage.

In particular embodiments, I/O interface 1408 includes hardware, software, or both, providing one or more interfaces for communication between computer system 1400 and one or more I/O devices. Computer system 1400 may include one or more of these I/O devices, where appropriate. One or more of these I/O devices may enable communication between a person and computer system 1400. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 1408 for them. Where appropriate, I/O interface 1408 may include one or more device or software drivers enabling processor 1402 to drive one or more of these I/O devices. I/O interface 1408 may include one or more I/O interfaces 1408, where appropriate. Although this disclosure describes and illustrates a particular I/O interface, this disclosure contemplates any suitable I/O interface.

In particular embodiments, communication interface 1410 includes hardware, software, or both providing one or more interfaces for communication (such as, for example, packet-based communication) between computer system 1400 and one or more other computer systems 1400 or one or more networks. As an example and not by way of limitation, communication interface 1410 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 1410 for it. As an example and not by way of limitation, computer system 1400 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 1400 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 1400 may include any suitable communication interface 1410 for any of these networks, where appropriate. Communication interface 1410 may include one or more communication interfaces 1410, where appropriate. Although this disclosure describes and illustrates a particular communication interface, this disclosure contemplates any suitable communication interface.

In particular embodiments, bus 1412 includes hardware, software, or both coupling components of computer system 1400 to each other. As an example and not by way of limitation, bus 1412 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 1412 may include one or more buses 1412, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Miscellaneous

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. Additionally, although this disclosure describes or illustrates particular embodiments as providing particular advantages, particular embodiments may provide none, some, or all of these advantages.

What is claimed is:

1. A method comprising:
outputting, by cycling a plurality of optical transmitters of an electronic device through different configurations of active transmitters, a plurality of optical signals from the plurality of optical transmitters into a portion of a user's body;
detecting, by a plurality of optical sensors of the electronic device during the cycling of the plurality of optical transmitters through different configurations of active transmitters, a plurality of deflected optical signals corresponding to the plurality of optical signals, the plurality of optical transmitters and optical sensors being positioned on the electronic device in a matrix configuration comprising a plurality of rows of the optical sensors with the optical transmitters placed between the optical sensors within the matrix configuration;
determining a plurality of spatial patterns of diffusion based on the plurality of deflected optical signals;
detecting a bone structure of the user's body based on the plurality of spatial patterns of diffusion; and
determining, based on the detected bone structure, a position of the electronic device relative to the user's body.

2. The method of claim 1, wherein the plurality of optical signals are outputted by a plurality of light sources that emit light, and
wherein the plurality of deflected optical signals are detected by a plurality of light sensors.

3. The method of claim 2, wherein outputting the plurality of optical signals by the plurality of light sources comprises outputting light in a plurality of wavelengths within a predefined optical range.

4. The method of claim 3, wherein the plurality of wavelengths are within an optical window between 750 nm to 950 nm.

5. The method of claim 1, further comprising:
determining a slippage position of the electronic device from a predefined position;
generating frame-of-reference data based on the slippage position; and
applying the frame-of-reference data to normalize data received from the electronic device.

6. The method of claim 5, wherein the predefined position comprises a position of the electronic device relative to a location of at least one of a radius bone and an ulna bone in a wrist area of the user's body.

7. The method of claim 6, further comprising, in response to a detection of a gesture made by the user:
determining a target area based on the frame-of-reference data;
selecting one or more of the plurality of optical transmitters substantially above or adjacent to the target area;
outputting one or more of the plurality of optical signals from the one or more selected optical transmitters; and
detecting a pattern of diffusion of the emitted light from the one or more selected optical transmitters.

8. The method of claim 7, wherein the target area comprises a target tendon area on a wrist area of the user's body.

9. The method of claim 1, wherein the electronic device comprises a wearable device.

10. The method of claim 9, wherein the detected bone structure is indicative of a portion of the user's body on which the wearable device is worn.

11. The method of claim 1, wherein detecting a bone structure of the user's body comprises detecting one or more of:
one or more bone characteristics,
one or more spatial locations of one or more bones of the detected bone structure, or
one or more characteristics of body tissue adjacent the one or more bones.

12. The method of claim 11, further comprising:
generating a bone-characteristic profile for the user based on one or more of the one or more bone characteristics, the one or more spatial locations of the one or more bones, or the one or more characteristics of the body tissue adjacent to the one or more bones; and
using the bone-characteristic profile to authenticate the user.

13. The method of claim 12, further comprising:
accessing a database comprising data on bone characteristics, spatial locations of one or more bones, and characteristics of body tissue adjacent one or more bones for a plurality of users, the data being organized into a plurality of user-profile clusters;
classifying the one or more bone characteristics, the one or more spatial locations of the one or more bones, or the one or more characteristics of the body tissue adjacent the one or more bones of the user as being associated with one or more of the plurality of user-profile clusters; and
generating a user profile for the user based on the classification.

14. The method of claim 1, further comprising:
prior to outputting the plurality of optical signals, determining one or more calibration parameters associated with the user; and
determining the position of the electronic device relative to the user's body based on characteristics of the detected bone structure and the one or more calibration parameters.

15. The method of claim 14, wherein the calibration parameters are determined by a calibration process comprising:
detecting characteristics of the detected bone structure for one or more predefined user gestures; and
generating normalization data based on the detected characteristics of the detected bone structure for the one or more predefined user gestures,
wherein the one or more calibration parameters are determined based on the characteristics of the detected bone structure and the normalization data.

16. The method of claim 15, further comprising, when a gesture made by the user is detected:
determining spatial locations of one or more bones of the detected bone structure to generate frame-of-reference data;
determining characteristics of body tissue adjacent the one or more bones; and
determining an estimated gesture based on a classification algorithm using the calibration parameters, the frameof-reference data, and the characteristics of the body tissue adjacent the one or more bones.

17. The method of claim 16, wherein the characteristics of body tissue adjacent the one or more bones comprises tendon characteristics during the detection of the gesture.

18. One or more computer-readable non-transitory storage media embodying software that is operable when executed to:
output, by cycling a plurality of optical transmitters of an electronic device through different configurations of active transmitters, a plurality of optical signals from the plurality of optical transmitters into a portion of a user's body;
detect, by a plurality of optical sensors of the electronic device during the cycling of the plurality of optical transmitters through different configurations of active transmitters, a plurality of deflected optical signals corresponding to the plurality of optical signals, the plurality of optical transmitters and optical sensors being positioned on the electronic device in a matrix configuration comprising a plurality of rows of the optical sensors with the optical transmitters placed between the optical sensors within the matrix configuration;
determine a plurality of spatial patterns of diffusion based on the plurality of deflected optical signals;
detect a bone structure of the user's body based on the plurality of spatial patterns of diffusion; and
determine, based on the detected bone structure, a position of the electronic device relative to the user's body.

19. A system comprising: one or more processors; and a non-transitory memory coupled to the processors comprising instructions executable by the processors, the processors operable when executing the instructions to:
output, by cycling a plurality of optical transmitters of an electronic device through different configurations of active transmitters, a plurality of optical signals from the plurality of optical transmitters into a portion of a user's body;
detect, by a plurality of optical sensors of the electronic device during the cycling of the plurality of optical transmitters through different configurations of active transmitters, a plurality of deflected optical signals corresponding to the plurality of optical signals, the plurality of optical transmitters and optical sensors being positioned on the electronic device in a matrix configuration comprising a plurality of rows of the optical sensors with the optical transmitters placed between the optical sensors within the matrix configuration;
determine a plurality of spatial patterns of diffusion based on the plurality of deflected optical signals;
detect a bone structure of the user's body based on the plurality of spatial patterns of diffusion; and
determine, based on the detected bone structure, a position of the electronic device relative to the user's body.

* * * * *